US008455453B2

(12) United States Patent  (10) Patent No.: US 8,455,453 B2
Alitalo et al.  (45) Date of Patent: Jun. 4, 2013

(54) USE OF VEGF-D GENE TO PREVENT RESTENOSIS

(75) Inventors: Kari Alitalo, Espoo (FI); Seppo Ylä-Herttuala, Kuopio (FI); Mikko O. Hiltunen, Kuopio (FI); Markku M. Jeltsch, Helsinki (FI); Marc G. Achen, North Melbourne (AU)

(73) Assignee: Vegenics Pty Ltd, Toorak, Victoria (AU)

( * ) Notice: Subject to any disclaimer, the term of this patent is extended or adjusted under 35 U.S.C. 154(b) by 1738 days.

(21) Appl. No.: 11/064,769

(22) Filed: Feb. 24, 2005

(65) Prior Publication Data

US 2005/0256075 A1  Nov. 17, 2005

Related U.S. Application Data

(63) Continuation of application No. 09/427,657, filed on Oct. 26, 1999, now Pat. No. 6,958,147.

(60) Provisional application No. 60/105,587, filed on Oct. 26, 1998.

(51) Int. Cl.
*A61K 48/00* (2006.01)
*C12N 15/00* (2006.01)
*C12N 15/09* (2006.01)
*C12N 15/11* (2006.01)

(52) U.S. Cl.
USPC ........... 514/44; 435/455; 435/69.1; 536/23.1; 536/23.2

(58) Field of Classification Search
None
See application file for complete search history.

(56) References Cited

U.S. PATENT DOCUMENTS

| | | | |
|---|---|---|---|
| 5,087,244 A | 2/1992 | Wolinsky et al. | |
| 5,631,237 A | 5/1997 | Dzau et al. | |
| 5,652,225 A | 7/1997 | Isner | |
| 5,653,689 A | 8/1997 | Buelna et al. | |
| 5,674,192 A | 10/1997 | Sahatjian et al. | |
| 5,679,400 A | 10/1997 | Tuch | |
| 5,697,967 A | 12/1997 | Dinh et al. | |
| 5,700,286 A | 12/1997 | Tartaglia et al. | |
| 5,707,385 A | 1/1998 | Williams | |
| 5,713,860 A | 2/1998 | Kaplan et al. | |
| 5,749,848 A | 5/1998 | Jang et al. | |
| 5,776,184 A | 7/1998 | Tuch | |
| 5,776,755 A | 7/1998 | Alitalo et al. | |
| 5,779,729 A | 7/1998 | Severini et al. | |
| 5,785,965 A | 7/1998 | Pratt et al. | |
| 5,792,453 A | 8/1998 | Hammond et al. | |
| 5,795,898 A | 8/1998 | Brown et al. | |
| 5,799,384 A | 9/1998 | Schwartz et al. | |
| 5,800,507 A | 9/1998 | Schwartz | |
| 5,824,048 A | 10/1998 | Tuch | |
| 5,830,879 A | 11/1998 | Isner | |
| 5,924,048 A | 7/1999 | McCormack et al. | |
| 5,932,540 A | 8/1999 | Hu et al. | |
| 5,935,820 A | 8/1999 | Hu et al. | |
| 5,994,300 A | 11/1999 | Bayne et al. | |
| 6,040,157 A | 3/2000 | Hu et al. | |
| 6,121,246 A | 9/2000 | Isner | |
| 6,235,713 B1 * | 5/2001 | Achen et al. | 514/12 |
| 6,338,709 B1 * | 1/2002 | Geoffrion et al. | 600/3 |
| 6,583,276 B1 * | 6/2003 | Neufeld et al. | 536/23.5 |
| 6,828,426 B1 * | 12/2004 | Hirata et al. | 530/399 |

FOREIGN PATENT DOCUMENTS

| | | |
|---|---|---|
| WO | WO-9524473 | 9/1995 |
| WO | WO-9624473 | 8/1996 |
| WO | WO-9639515 | 12/1996 |
| WO | WO-9705250 | 2/1997 |
| WO | WO-9709427 | 3/1997 |
| WO | WO-9717359 | 5/1997 |
| WO | WO-9717442 | 5/1997 |
| WO | WO-9807832 | 2/1998 |
| WO | WO-9819712 | 5/1998 |
| WO | WO-9820027 | 5/1998 |
| WO | WO-9824811 | 6/1998 |
| WO | WO-9833917 | 8/1998 |
| WO | WO-9849300 | 11/1998 |
| WO | WO-9907844 | 2/1999 |

OTHER PUBLICATIONS

Raper, Surgery, 137(5):487-492, 2005.*
Kimmelman, BMJ, 220:79-82, 2003.*
Juengst, BMJ, 326:1410-1411, 2003.*
Wolf, Nat. Biotechnol. 20:768-769, 2002.*
Rosenberg et al, Science 287:1751, 2000.*
Donsante et al, Science, 317:477, 2007.*
Couzin et al, Science 307:1028, 2005.*
Touchette, Nat. Med. 2(1):7-8, 1996.*
Rutanen et al, Gene Therapy 12:980-987,2005.*
Thomas et al, Progress and Problems With the Use of Viral Vectors for Gene Therapy, Nature, 346 I May 2003, vol. 4, pp. 346-358.*
Russell, S. J., Replicating Vectors for Gene Therapy of Cancer: Risks, Limitations and Prospects, European J Cancer, 1994, vol. 30A (8), pp. 1165-1171.*
Check, E, Cancer fears cast doubts on future of gene therapy, Nature,2003, Vo1421, p. 678.*
Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Murat Kasap, Phylogenetic Analysis of Vascular Endothelial Growth Factor Diversity, Turk J Biol 29 (2005) 217-227.*
Leppanen et al, Structural determinants of vascular endothelial growth factor-D receptor binding and specificity, Blood, Feb. 3, 2011 _vol. 117, No. 5, 1507-1515.*
Enholm, et al., "Vascular endothelial growth factor C, a growth factor for lymphatic endothelial cells," Trends in Cardiovascular Med. 8:292 297 (1998).
Enholm, et al., "Comparison of VEGF, VEGF B, VEGF C and Ang 1 mRNA regulation by serum, growth factors, oncoproteins and hypoxia," Oncogene 14:2475 2483 (1997).
Feldman, et al., "Perspectives of arterial gene therapy for the prevention of restenosis," Cardiovascular Research 32:194 207 (1996).

(Continued)

Primary Examiner — Maria Marvich
(74) Attorney, Agent, or Firm — Marshall, Gerstein & Borun LLP

(57) ABSTRACT

The present invention provides materials and methods for preventing stenosis or restenosis of a blood vessel using Vascular Endothelial Growth Factor C (VEGF-C) and/or Vascular Endothelial Growth Factor D (VEGF-D) genes or proteins.

46 Claims, 4 Drawing Sheets

OTHER PUBLICATIONS

Ferrara, et al., "Clinical applications of angiogenic growth factors and their inhibitors," Nature Med 5:1359 64 (Dec. 1999).
GenBank Accession No. AJ000185 *Homo sapiens* mRNA for vascular endothelial growth factor D.
GenBank Accession No. AF014827 *Rattus norvegicus* vascular endothelial growth factor D (VEGF D) mRNA, complete cds.
GenBank Accession No. MMU73620 *Mus musculus* VEGF C mRNA, complete cds.
GenBank Accession No. CCY15837 Coturnix coturnix mRNA for vascular endothelial growth factor C.
GenBank Accession No. D89628 *Mus musculus* mRNA for vascular endothelial growth factor D, complete cds.
GenBank Accession No. X94216 *H. sapiens* mRNA for VEGF C protein.
Gnatenko, et al., "Characterization of recombinant adeno associated virus 2 as a vehicle for gene delivery and expression into vascular cells," J. Investig. Med. 45:87 89 (1997).
Grosskreutz, et al., "Vascular endothelial growth factor induced migration of vascular smooth muscle cells in vitro," Microvasc. Res. 58(2):128 136 (1999).
Hu, et al., "A novel regulatory function of proteolytically cleaved VEGF 2 for vascular endothelial and smooth muscle cells," FASEB J. 11:498 504 (1997).
International Search Report for PCT/US99/24054.
Isner, et al., "Arterial gene therapy for therapeutic angiogenesis in patients with peripheral artery disease," Circulation 91:2687 2692 (1995).
Isner, et al., "Arterial gene therapy for restenosis," Human Gene Therapy 7:989 1011 (May 1996).
Jeltsch, et al., "Hyperplasia of lymphatic vessels in VEGF C transgenic mice," Science 276:1423 1425 (1997).
Joukov, et al., "Vascular endothelial growth factors VEGF B and VEGF C," J. Cell Physiol 173:211 215 (1997).
Joukov, et al., "Proteolytic processing regulates receptor specificity and activity of VEGF C," EMBO J. 16(13):3898 3911 (1997).
Joukov, et al., "A recombinant mutant vascular endothelial growth factor C that has lost vascular endothelial growth factor receptor 2 binding, activation, and vascular permeability activities," J. Biol. Chem. 273(12):6599 6602 (Mar. 1998).
Joukov, et al., "A novel vascular endothelial growth factor, VEGF C, is a ligand for the Flt4 (VEGFR 3) and KDR (VEGFR 2) receptor tyrosine kinases," EMJO J. 15:290 298 (1996).
Jussila, et al., "*Lymphatic endothelium* and *Kaposi's sarcoma* spindle cells detected by antibodies against the vascular endothelial growth factor receptor 3," Cancer Res. 58(8):1599 604 (1998).
Kagan, et al., "Mediators of restenosis," Surgical Clinics of North America 78:481 500 (Jun. 1998).
Kim, et al., "Minimal requirements for lentivirus vector based on human immunodeficiency virus type 1," J. Virol. 72(1):811 816 (Jan. 1998).
Kingsman et al., "A new generation of gene therapy vectors," Scrip Magazine 43 46 (Oct. 1998).
Ark Therapeutics Group PLC—Research Update, Ark's VEGF D gene-based medicine to commence Phase I/IIa development in refractory angina, Aug. 26, 2009.
Ark Therapeutics Group PLC—Trinam Phase III Study Enrolls First Patient, Trinam® Phase III Study Enrols First Patient, May 21, 2009.
Ark Therapeutics Group PLC—Trinam Phase III trial to commence, Ark completes potency test qualification enabling Trinam® Phase III trial to commence, Jan. 8, 2009.
Ark Therapeutics Ltd., Adenoviral Vascular Endothelial Growth Factor (VEGF) Therapy in Vascular Access—Novel Trinam Against Control Evidence (AdV-Vantage), <http://clinicaltrials.gov/ct2/show/record/NCT00895479> Sep. 15, 2009.
Bell et al., Human epidermal growth factor precursor: cDNA sequence, expression in vitro and gene organization. *Nucl. Acids Res.* 14(21): 8427-46 (1986).
Bhardwaj et al., VEGF-A, VEGF-D and VEGF-D(DeltaNDeltaC) induced intimal hyperplasia in carotid arteries. *Eur. J. Clin. Invest.* 35(11): 669-76 (2005).
Chicago Tribune, May 10, 2002, Section 3, p. 4.
Corson et al., Fibrillin binds calcium and is coded by cDNAs that reveal a multidomain structure and alternatively spliced exons at the 5' end. *Genomics*, 17: 476-84 (1993).
Dangas et al., Restenosis: Repeat Narrowing of a Coronary Artery: Prevention and Treatment. *Circulation*, 105: 2586-7 (2002).
Kaipainen et al., Expression of the fms-like tyrosine kinase 4 gene becomes restricted to lymphatic endothelium during development. *Proc. Natl. Acad. Sci. USA.* 92: 3566-70 (1995).
Kingsley, The TGF-beta superfamily: New members, new receptors, and new genetic tests of function in different organisms. *Genes & Development*, 8(2): 133-46 (1994).
Lawson, New Directions in Dialysis Access: Genes, Cells, Wraps . . . Stents, Struts, PTFE and Plastic presentation notes.
Losordo et al., Phase 1/2 placebo-controlled, double-blind, dose-escalating trial of myocardial vascular endothelial growth factor 2 gene transfer by catheter delivery in patient with chronic myocardial ischemia. *Circulation*, 105: 2012-8 (2002).
Massague, The transforming growth factor-beta family. *Annu. Rev. Cell. Biol.* 6: 597-641 (1990).
Parfyonova et al., Plasminogen activators in vascular remodeling and angiogenesis. *Biochemistry* (Moscow), 67(1): 119-34 (2002).
Rissanen et al., Current status of cardiovascular gene therapy. *Molec. Ther.* 15(7): 1233-47 (2007).
Rissanen et al., VEGF-D is the strongest angiogenic and lymphangiogenic effector among VEGFs delivered into skeleton muscle via adenoviruses. *Circ. Res.* 92: 1098-106 (2003).
Rutanen et al., Adenoviral catheter-mediated intrmyocardial gene transfer using the mature form of vascular endothelial growth factor-D induces transmural angiogenesis in porcine heart. *Circulation*, 209: 1029-35 (2004).
Saaristo et al., Vascular endothelial growth factor-C gene therapy restores lymphatic flow across incision wounds. *FASEB J.* Sep. 10, 2004.
Vale et al., Randomized, single-blind, placebo-controlled pilot study of catheter-based myocardial gene transfer for therapeutic angiogenesis using left ventricular electromechanical mapping in patients with chronic myocardial ischemia. *Circulation*, 103: 2138-43 (2001).
Anderson, Human gene therapy. *Nature*, 392: 25-30 (1998).
Crystal, Transfer of genes to humans: Early lessons and obstacles to success. *Science*, 270: 404-10 (1995).
Deonarain et al., Ligand-targeted receptor-mediated vectors for gene delivery. *Exp. Opin. Ther. Patents*, 8(1): 53-69 (1998).
Eck et al., Gene-based therapy. Goodman & Gilman's The Pharmacological Basis of Therapeutics, 9$^{th}$ Edition, McGraw Hill: 77-101 (1996).
Friedmann, Principles for human gene therapy studies. *Science*, 287(5461): 2163-5 (2000).
Hiltunen et al., Intravascular adenovirus-mediate VEGF-C gene transfer reduces neointima formation in balloon-denuded rabbit aorta. *Circulation*, 102: 2262-8 (2000).
Miller et al., Targeted vestors for gene therapy. *FASEB*, 9: 190-9 (1995).
Ngo, Computational complexity protein structure prediction and the Levinthal paradox in the protein folding problem and tertiary structure prediction. Merz et al., (Eds.), Birkhauser Boston: Boston, MA, pp. 433 and 492-495 (1994).
Rosenberg et al., Gene Therapist, Heal Thyself. *Science.* 287: 1751 (2000).
Rudinger Characteristics of amino acids as components of a peptide hormone sequence in Peptide Hormones, Parsons (Ed.), University Park Press: Baltimore, MD, pp. 1-7 (1976).
Touchette et al., Gene therapy: Not ready for prim time. *Nat. Med.* 2(1): 7-8 (1996).
Turunen et al., Gene therapy for angiogenesis, restenosis, and related diseases. *Exp. Gerontol.* 43(4): 567-74 (1999).
Verma et al., Gene therapy-promises, problems and prospects. *Nature*, 389: 239-42 (1997).
Verma, Gene therapy: Beyond 2000. *Mol. Ther.* 1: 493 (2000).
Witzenbichler et al., Vascular endothelial growth factor-C (VEGF-C/VEGF-2) promotes angiogenesis in the setting of tissue ischemia. *Am. J. Pathol.* 153(2): 381-94 (1998).

Achen, M.G. et al., "Vascular endothelial growth factor D (VEGF D) is a ligand for the tyrosine kinases VEGF receptor 2 (Flk1) and VEGF receptor 3 (Flt4)," Proc. Natl. Acad. Sci. USA 95(2):548 553 (Jan. 1998).

Alitalo et al., "Vascular Endothelial Growth Factors B and C and Receptors Involved in Angiogenesis," German American Academic Council Foundation (GAAC)/ Stiftung Deutsch Amerikanisches Akademisches Konzil (DAAK), 2nd Symposium on Current Problems in Molecular Medicine: The Role of Cytokines in Human Disease, Nov. 17 20, 1996, Ringberg Castle, Germany, p. 1 (Abstract).

Asahara, et al., "Accelerated restitution of endothelial integrity and endothelium dependent function after phVEGF165 gene transfer," Circulation 94:3291 3302 (1996).

Asahara, et al., "Local delivery of vascular endothelial growth factor accelerates reendothelialization and attenuates intimal hyperplasia in balloon injured rat carotid artery," Circulation 91:2793 2801 (1995).

Barr, et al., "Efficient catheter mediated gene transfer into the heart using replication defective adenovirus," Gene Ther. 1:51 58 (1994).

Boshart, et al., "A very strong enhancer is located upstream of an immediate early gene of human cytomegalovirus," Cell 41:521 530 (Jun. 1985).

Callow, et al., "Vascular permeability factor accelerates endothelial regrowth following balloon angioplasty," Growth Factors 10:223 228 (1994).

Camenzind et al., "Use of Locally Delivered Conventional Drug Therapies," Semin Intervent Cardiol 1:67 76 (1996).

Cao, et al., "Vascular endothelial growth factor C induces angiogenesis in vivo," Proc. Natl. Acad. Sci. 95:14389 14394 (1998).

Cerek, et al., "Growth factors in pathogenesis of coronary arterial restenosis," Am. J. Cardiol. 68:24C 33C (Nov. 1991).

Chang, et al., "Gene therapy for vascular proliferative disorders," Semin. Intervent. Cardiol. 1:185 193 (1996).

Darius, et al., "Lokale Medikamentengabe und Gentherapie," Herz 22:347 54 (1997).

Davis, et al., "Direct gene transfer into skeletal muscle in vivo: factors affecting efficiency of transfer and stability of expression," Hum. Gene Ther. 4:151 9 (1993).

Debbas, et al., "Stenting within a stent: Treatment, for repeat in stent restenosis in a venous graft," American Heart Journal 133:460 468 (Apr. 1997).

De Meyer, et al., "Mechanisms of neointima formation lessons from experimental models," Vasc. Med. 2:179 189 (1997).

DeYoung, et al., "Gene therapy for restenosis: Are we ready?," Circ. Res. 82:306 313 (1998).

Dignam, et al., "Balbiani ring 3 in *Chironomus tentans* encodes a 185 kDa secretory protein which is synthesized throughout the fourth larval instar," Gene 88:133 140 (1990).

Korhonen, et al., "Endothelial specific gene expression directed by the tie gene promoter in vivo," Blood 86(5):1828 1835 (Sep. 1995).

Kukk, et al., "VEGF C receptor binding and pattern of expression with VEGFR 3 suggests a role in lymphatic vascular development," Development 122:3829 3839 (1996).

Laitinen, et al., "VEGF gene transfer reduces intimal thickening via increased production of nitric oxide in carotid arteries," Hum. Gene Ther 8:1737 1744 (Oct. 1997).

Laitinen, et al., "Adenovirus mediated gene transfer to lower limb artery of patients with chronic critical leg ischemia," Hum. Gene Ther. 9:1481 1486 (Jul. 1998).

Laitinen, et al., "Adventitial gene transfer to arterial wall," Pharmacol Res 37:251 254 (1998).

Lambert, et al., "Local drug delivery catheters: functional comparison of porous and microporous designs," Coron. Artery Dis. 4:469 475 (1993).

Lee, et al., "Vascular endothelial growth factor related protein: A ligand and specific activator of the tyrosine kinase receptor Flt4," Proc. Natl. Acad. Sci. USA 93:1988 1992 (1996).

Lehner, et al., "Comparative sequence analysis of human cytomegalovirus strains," J. Clin. Microbiol. 29:2494 2502 (Nov. 1991).

Libby, "Gene therapy of restenosis: Promise and Perils," Circ. Res. 82:404 406 (1998).

Lincoff, et al., "Local drug delivery for the prevention of restenosis: Fact, Fancy, and Future," Circulation 90:2070 2084 (1994).

Lymboussaki, et al., "Expression of the vascular endothelial growth factor C receptor VEGFR 3 in lymphatic endothelium of the skin and in vascular tumors," Am J. Path 153:395 403 (Aug. 1998).

Marchió, et al., "Vascular endothelial growth factor C stimulates the migration and proliferation of *Kaposi's sarcoma* cells," J. Biol. Chem. 274:27617 27622 (Sep. 1999).

Mazur, et al., "Coronary restenosis and gene therapy," Texas Heart Institute Journal 21:104 111 (1994).

Morishita, et al., "Contribution of a vascular modulator, hepatocyte growth factor (HGF), to the pathogenesis of cardiovascular disease," J. Atherosclerosis and Thrombosis 4(3):128 134 (1998).

Mulligan, "The basic science of gene therapy," Science 260:926 932 (May 1993).

Narins, et al., "A call for provisional stenting: The balloon in back," Circulation 97:1298 1305 (1998).

Oh, et al., "VEGF and VEGF C: Specific induction of angiogenesis and lymphangiogenesis in the differentiated avian chorioallantoic membrane," Dev. Biol. 188:96 109 (1997).

Ohno, et al., "Gene therapy for vascular smooth muscle cell proliferation after arterial injury," Science 265:781 784 (Aug. 1994).

Paavonen et al., "Chromosomal Localization and Regulation of Human Vascular Endothelial Growth Factors B and C (VEGF B and VEGF C)," IX International Vascular Biology Meeting, Seattle, Washington, Sep. 4-8, 1996, p. 76 (Abstract 299).

Paavonen et al., "Novel Human Vascular Endothelial Growth Factor Genes VEGF B and VEGF C Localize to Chromosomes 11q13 and 4q34, Respectively," Circulation 93(6):1079 1082 (Mar. 15, 1996).

Paulsson, et al., "The Balbiani ring 3 gene in Chironomus tentans has diverged repetitive structure split by many introns," J. Mol. Biol. 211:331 349 (1990).

Pepper, et al., "Vascular endothelial growth factor (VEGF) C synergizes with basic fibroblast growth factor and VEGF in the induction of angiogenesis in vitro and alters endothelial cell extracellular proteolytic activity," J. Cell Physiol. 177:439 452 (1998).

Quantin, et al., "Adenovirus as an expression vector in muscle cells in vivo," Proc. Natl. Acad. Sci. USA 89:2581 2584 (Apr. 1992).

Riessen, et al., "Arterial gene transfer using pure DNA applied directly to a hydrogel coated angioplasty balloon," Human Gene Therapy 4:749 758 (1993).

Riessen, et al, "Prospects for site specific delivery of pharmacologic and molecular therapies," J. Am. Coll. Cardiol. 23:1234 1244 (Apr. 1994).

Rosenfeld, et al., "In vivo transfer of the human cystic fibrosis transmembrane conductance regulator gene to the airway epithelium," Cell 68:143 155 (Jan. 1992).

Salven, et al., "Vascular endothelial growth factors VEGF B and VEGF C are expressed in human tumors," Am. J. Pathol. 153:103 108 (1998).

Sambrook et al., Molecular Cloning: A Laboratory Manual, 2nd ed., Cold Spring Harbor Laboratory Press, § 9.47 9.51 (1989).

Schwartz, "The vessel wall reaction in restenosis," Semin Intervent Cardiol 2:83 88 (1997).

Serruys, et al., "Heparin coated Palmaz Schatz stents in human coronary arteries," Circulation 93:412 422 (1996).

Shih, et al., "Focal accumulation of an apolipoprotein B based synthetic oligopeptide in the healing rabbit arterial wall," Proc Natl. Acad Sci. USA 87:1436 1440 (Feb. 1990).

Steg, et al., "Arterial gene transfer to the rabbit endothelial and smooth muscle cells using percutaneous delivery of an adenoviral vector," Circulation 90:1648 1656 (1994).

Steg, et al., "Reduction of restenosis after angioplasty in a atheromatous rabbit model by suicide gene therapy," Circulation 96:408 411 (1997).

Stratford Perricaudet, et al., "Widespread long term gene transfer to mouse skeletal muscles and heart," J. Clin. Invest. 90:626 630 (Aug. 1992).

Turunen, et al., Efficient adventitial gene delivery to rabbit carotid artery with cationic polymer plasmic complexes, Gene Therapy 6:6 11 (1999).

Van Belle, et al., "Passivation of metallic stents after arterial gene transfer of phVEGF165 inhibits thrombus formation and intimal thickening," J. Am. Coll. Cardiol. 29:1371 1379 (May 1997).

Valtola, et al., "VEGFR 3 and its ligand VEGF C are associated with angiogenesis in breast cancer," Am. J. Pathol. 154:1381 1390 (May 1999).

Wang, et al., "Signal transduction in human hematopoietic cells by vascular endothelial growth factor related protein, a novel ligand for the FLT4 receptor," Blood 90(9):3507 15 (1997).

Wartiovaara, et al., "Peripheral blood platelets express VEGF C and VEGF which are released during platelet activation," Thromb. Haemost. 80:171 175 (1998).

Wilensky, et al., "Methods and devices for local drug delivery in coronary and peripheral arteries," Trends Cardiovasc. Med. 3:163 170 (1993).

Willard, et al., "Genetic modification of the vessel wall," Circulation 89:2190 2197 (1994).

Witzenbichler, et al., "Bioactivity of vascular endothelial growth factor 2 (=VEGF C) in vitro and in vivo following intraarterial administration of recombinant protein or intravascular gene transfer in a rabbit ischemic hindlimb model," Eur Heart J. 18:suppl. p. 5 (1997).

Wolinsky, et al., "Use of a perforated balloon catheter to deliver concentrated heparin into the wall of the normal canine artery," J. Am. Coll. Cardiol. 15:475 481 (Feb. 1990).

Ylä Herttuala, et al., "Biochemical composition of coronary arteries in Finnish children," Arteriosclerosis 6:230 236 (Mar./Apr. 1986).

Ylä Herttuala, "Gene therapy for cardiovascular diseases," Ann Med 28:89 93 (1996).

Ylä Herttuala, "Vascular gene transfer," Curr Opin Lipidol 8:72 76 (1997).

\* cited by examiner

USE OF VEGF-D GENE TO PREVENT RESTENOSIS

This application is a continuation of U.S. patent application Ser. No. 09/427,657, filed Oct. 26, 1999, now U.S. Pat. No. 6,958,147, which claims the priority benefit of U.S. Provisional Application No. 60/105,587, filed Oct. 26, 1998. All priority applications are incorporated herein by reference.

FIELD OF THE INVENTION

The present invention provides materials and methods to prevent stenosis and restenosis of blood vessels, and relates generally to the field of cardiovascular medicine.

BACKGROUND OF THE INVENTION

Coronary artery disease constitutes a major cause of morbidity and mortality throughout the world, especially in the United States and Europe. Percutaneous transluminal coronary angioplasty (e.g., balloon angioplasty, with our without intracoronary stenting) is now a common and successful therapy for such disease, performed hundreds of thousands of times per year in the United States alone. However, restenosis occurs in as many as one-third to one-half of such revascularization procedures, usually within six months of the angioplasty procedure. The economic cost of restenosis has been estimated at $2 billion annually in the United States alone. [Feldman et al., *Cardiovascular Research*, 32: 194-207 (1996), incorporated herein by reference.] Autopsy and atherectomy studies have identified intimal hyperplasia as the major histologic component of restenotic lesions. [Cerek et al., *Am. J. Cardiol.*, 68: 24C-33C (1991).]

Restenosis also remains a clinical concern in angioplasty that is performed in peripheral blood vessels. Likewise, stenosis is a clinical concern following transplantation of blood vessels (e.g., grafted veins and grafted artificial vessels) for cardiac bypass therapy or for treatment of peripheral ischemia or intermittent claudication, for example (e.g., above-knee femoro-popliteal arterial bypass grafts).

Mazur et al., *Texas Heart Institute Journal*, 21; 104-111 (1994) state that restenosis is primarily a response of the artery to the injury caused by percutaneous coronary angioplasty, which disrupts the intimal layer of endothelial cells and underlying smooth muscle cells of the media. The authors state that multiple growth factors secreted by platelets, endothelial cells, macrophages, and smooth muscle cells are mechanistically involved in the restenosis process, and that proliferation of smooth muscle cells constitutes a critical pathogenetic feature. According to the authors, this smooth muscle cell proliferation has proven refractory to mechanical and pharmacologic therapy. More recently, others have called into question whether smooth muscle cell proliferation is of penultimate importance in restenosis. See Libby, *Circ. Res.*, 82: 404-406 (1998).

Narins et al, *Circulation*, 97: 1298-1305 (1998) review the use of intracoronary stents and their benefits and limitations in preventing restenosis. Debbas et al., *American Heart Journal*, 133: 460-468 (1997) discuss stenting within a stent to treat in-stent restenosis.

Chang & Leiden, *Semin. Intervent. Cardiol.*, 1: 185-193 (1996), incorporated herein by reference, review somatic gene therapy approaches to treat restenosis. Chang and Leiden teach that replication-deficient adenoviruses comprise a promising and safe vector system for gene therapy directed toward prevention of restenosis, because such viruses can efficiently infect a wide variety of cell types, including vascular smooth muscle cells; such viruses can be produced at high titers (e.g., $10^{10}$-$10^{12}$ plaque forming units per milliliter); such viruses can accommodate a transgene insert of, e.g., 7-9 kilobases (kb) in size; such viruses can be delivered percutaneously through standard catheters; and such viruses do not integrate into the host genome. Both Chang & Leiden and Feldman et al., supra, also review cytotoxic and cytostatic gene therapy approaches, designed to kill or arrest proliferating vascular smooth muscle cells thought to be responsible for neointimal formations that characterize restenosis.

Riessen & Isner, *J. Am. Coll. Cardiol.*, 23:1234-1244 (1994), incorporated by reference, review devices for intravascular drug delivery and vectors for intravascular gene therapy.

Cerek et al., *Am. J. Cardiol.*, 68: 24C-33C (1991) suggest prevention of restenosis by inhibiting growth-factor-mediated healing of arterial injury. Potential roles of platelet-derived growth factor (PDGF), thrombospondin, insulin-like growth factor 1 (IGF-1), fibroblast growth factors (FGF's), transforming growth factor alpha (TGF-α) and beta (TGF-β), epidermal growth factor (EGF) are discussed.

Isner & Asahara, International Patent Publication No. WO 98/19712, incorporated herein by reference, suggest treating injured blood vessels and accelerating reendothelialization following angioplasty by isolating a patient's endothelial progenitor cells and re-administering such cells to the patient. The authors suggest that the effectiveness of using an angiogenesis-promoting growth factor, such as vascular endothelial growth factor (VEGF) or basic fibroblast growth factor (bFGF), may be limited by the lack of endothelial cells on which the VEGF or bFGF will exert its effect.

Martin et al., International Patent Publication No. WO 98/20027 suggest the use of VEGF gene or protein to treat or prevent stenosis or restenosis of a blood vessel. The authors suggest that any beneficial effect of VEGF arises from a different mechanism of action than the mechanism underlying an activity of VEGF related to stimulating re-endothelialisation in cases where the endothelium has been damaged.

Callow et al., *Growth Factors*, 10: 223-228 (1994) state that intravenous injection of vascular permeability factor (a.k.a. VEGF) into rabbits that had been subjected to balloon angioplasty-induced endothelial denudation resulted in increased regeneration of endothelium compared to a control. The authors also stated that basic fibroblast growth factor (bFGF) is effective at promoting re-endothelialization, but that such re-endothelialization is accompanied by increases in neointimal lesion size.

Asahara et al., *Circulation*, 94: 3291-3302 (Dec. 15, 1996) state that local, percutaneous catheter delivery of a CMV-human-VEGF$_{165}$ transgene achieved accelerated re-endothelialization in balloon-injured rabbits, and resulted in diminished intimal thickening. In a report by a related group of authors, Van Belle et al., *J. Am. Coll. Cardiol.*, 29:1371-1379 (May, 1997) state that stent endothelialization was accelerated by delivery of a CMV-human-VEGF$_{165}$ transgene and was accompanied by attenuation of intimal thickening.

Morishita et al., *J. Atherosclerosis and Thrombosis*, 4(3): 128-134 (1998) state that hepatocyte growth factor (HGF) has a mitogenic activity on human endothelial cells more potent than VEGF, and hypothesized that HGF gene therapy may have potential therapeutic value for the treatment of cardiovascular diseases such as restenosis after angioplasty. Morishita et al. also state that there is little knowledge about growth factors that stimulate only endothelial cells, but not vascular smooth muscle cells.

DeYoung & Dichek, *Circ. Res.*, 82: 306-313 (1998) state that VEGF gene delivery does not currently appear destined for application to human coronary restenosis, and that two independent studies suggest that VEGF delivery may actually worsen arterial intimal hyperplasia.

Brown et al., U.S. Pat. No. 5,795,898, suggest using an inhibitor of PDGF, FGF, EGF, or VEGF signaling to suppress accelerated atherogenesis involved in restenosis of coronary vessels or other arterial vessels following angioplasty.

The foregoing discussion demonstrates that a long-felt need continues to exist for improvements to angioplasty materials and/or methods, and/or for adjunct therapies, to reduce instances of restenosis.

SUMMARY OF THE INVENTION

The present invention addresses long-felt needs in the field of medicine by providing materials and methods for the prevention of stenosis or restenosis in mammalian blood vessels.

For example, the invention provides a method of treating a mammalian subject to prevent stenosis or restenosis of a blood vessel, comprising the step of administering to a mammalian subject in need of treatment to prevent stenosis or restenosis of a blood vessel a composition comprising a polynucleotide, the polynucleotide comprising a nucleotide sequence that encodes a vascular endothelial growth factor C (VEGF-C) polypeptide. In a preferred embodiment, the subject is a human subject.

While it is contemplated that the VEGF-C polynucleotide could be administered purely as a prophylactic treatment to prevent stenosis, it is contemplated in a preferred embodiment that the polynucleotide be administered shortly before, and/or concurrently with, and/or shortly after a percutaneous transluminal coronary angioplasty procedure, for the purpose of preventing restenosis of the subject vessel. In another preferred embodiment, the polynucleotide is administered before, during, and/or shortly after a bypass procedure (e.g., a coronary bypass procedure), to prevent stenosis or restenosis in or near the transplanted (grafted) vessel, especially stenosis at the location of the graft itself. In yet another embodiment, the polynucleotide is administered before, during, or after a vascular transplantation in the vascular periphery that has been performed to treat peripheral ischemia or intermittent claudication. By prevention of stenosis or restenosis is meant prophylactic treatment to reduce the amount/ severity of, and/or substantially eliminate, the stenosis or restenosis that frequently occurs in such surgical procedures. The polynucleotide is included in the composition in an amount and in a form effective to promote expression of a VEGF-C polypeptide in a blood vessel of the mammalian subject, thereby preventing stenosis or restenosis of the blood vessel.

In a preferred embodiment, the mammalian subject is a human subject. For example, the subject is a person suffering from coronary artery disease that has been identified by a cardiologist as a candidate who could benefit from a therapeutic balloon angioplasty (with or without insertion of an intravascular stent) procedure or from a coronary bypass procedure. Practice of methods of the invention in other mammalian subjects, especially mammals that are conventionally used as models for demonstrating therapeutic efficacy in humans (e.g., primate, porcine, canine, or rabbit animals), also is contemplated.

For the practice of methods of the invention, the term "VEGF-C polypeptide" is intended to include any polypeptide that has a VEGF-C or VEGF-C analog amino acid sequence (as defined elsewhere herein in greater detail) and that possesses in vivo restenosis-reducing effects of human VEGF-C, which effects are demonstrated herein by way of example in a rabbit model. The term "VEGF-C polynucleotide" is intended to include any polynucleotide (e.g., DNA or RNA, single- or double-stranded) comprising a nucleotide sequence that encodes a VEGF-C polypeptide. Due to the well-known degeneracy of the genetic code, there exist multiple VEGF-C polynucleotide sequences that encode any selected VEGF-C polypeptide.

For treatment of humans, VEGF-C polypeptides with an amino acid sequence of a human VEGF-C are highly preferred, and polynucleotides comprising a nucleotide sequence of a human VEGF-C cDNA are highly preferred. By "human VEGF-C" is meant a polypeptide corresponding to a naturally occurring protein (prepro-protein, partially-processed protein, or fully-processed mature protein) encoded by any allele of the human VEGF-C gene, or a polypeptide comprising a biologically active fragment of a naturally-occurring mature protein. By way of example, a human VEGF-C comprises a continuous portion of the amino acid sequence set forth in SEQ ID NO: 2 sufficient to permit the polypeptide to bind and stimulate VEGFR-2 and/or VEGFR-3 phosphorylation in cells that express such receptors. A polypeptide comprising amino acids 131-211 of SEQ ID NO: 2 is specifically contemplated. For example, polypeptides having an amino acid sequence comprising a continuous portion of SEQ ID NO: 2, the continuous portion having, as its amino terminus, an amino acid selected from the group consisting of positions 30-131 of SEQ ID NO: 2, and having, as its carboxyl terminus, an amino acid selected from the group consisting of positions 211-419 of SEQ ID NO: 2 are contemplated. As explained elsewhere herein in greater detail, VEGF-C biological activities, especially those mediated through VEGFR-2, increase upon processing of both an amino-terminal and carboxyl-terminal pro-peptide. Thus, an amino terminus selected from the group consisting of positions 102-131 of SEQ ID NO: 2 is preferred, and an amino terminus selected from the group consisting of positions 103-113 of SEQ ID NO: 2 is highly preferred. Likewise, a carboxyl terminus selected from the group consisting of positions 211-227 of SEQ ID NO: 2 is preferred. As stated above, the term "human VEGF-C" also is intended to encompass polypeptides encoded by allelic variants of the human VEGF-C characterized by the sequences set forth in SEQ ID NOs: 1 & 2.

Moreover, since the therapeutic VEGF-C is to be administered as recombinant VEGF-C or indirectly via somatic gene therapy, it is within the skill in the art to make and use analogs of human VEGF-C (and polynucleotides that encode such analogs) wherein one or more amino acids have been added, deleted, or replaced with other amino acids, especially with conservative replacements, and wherein the anti-restenosis biological activity has been retained. Analogs that retain anti-restenosis VEGF-C biological activity are contemplated as VEGF-C polypeptides for use in the present invention. In a preferred embodiment, analogs having 1, 2, 3, 4, 5, 6, 7, 8, 9, 10, 11, 12, 25 13, 14, 15, 16, 17, 18, 19, 20, 21, 22, 23, 24, or 25 such modifications and that retain anti-restenosis VEGF-C biological activity are contemplated as VEGF-C polypeptides for use in the present invention. Polynucleotides encoding such analogs are generated using conventional PCR, site-directed mutagenesis, and chemical synthesis techniques.

Also contemplated as VEGF-C polypeptides are non-human mammalian or avian VEGF-C polypeptides and polynucleotides. By "mammalian VEGF-C" is meant a polypeptide corresponding to a naturally occurring protein (prepro-protein, partially-processed protein, or fully-processed mature protein) encoded by any allele of a VEGF-C gene of any mammal, or a polypeptide comprising a biologically active fragment of a mature protein. The term "mammalian VEGF-C polypeptide" is intended to include analogs of mammalian VEGF-C's that possess the in vivo restenosis-reducing effects of the mammalian VEGF-C. The fact that gene therapy using a transgene encoding human VEGF-C is effective to prevent restenosis in a rabbit model is evidence of the inter-species therapeutic efficacy of VEGF-C proteins.

Irrespective of which VEGF-C polypeptide is chosen, the VEGF-C polynucleotide preferably comprises a nucleotide sequence encoding a secretory signal peptide fused in-frame with the VEGF-C polypeptide sequence. The secretory signal peptide directs secretion of the VEGF-C polypeptide by the cells that express the polynucleotide, and is cleaved by the cell from the secreted VEGF-C polypeptide. For example, the VEGF-C polynucleotide could encode the complete prepro-VEGF-C sequence set forth in SEQ ID NO: 2; or could encode the VEGF-C signal peptide fused in-frame to a sequence encoding a fully-processed VEGF-C (e.g., amino acids 103-227 of SEQ ID NO: 2) or VEGF-C analog. Moreover, there is no requirement that the signal peptide be derived from VEGF-C. The signal peptide sequence can be that of another secreted protein, or can be a completely synthetic signal sequence effective to direct secretion in cells of the mammalian subject.

In one embodiment, the VEGF-C polynucleotide of the invention comprises a nucleotide sequence that will hybridize to a polynucleotide that is complementary to the human VEGF cDNA sequence specified in SEQ ID NO: 1 under the following exemplary stringent hybridization conditions: hybridization at 42° C. in 50% formamide, 5X SSC, 20 mM Na—$PO_4$, pH 6.8; and washing in 1X SSC at 55° C. for 30 minutes; and wherein the nucleotide sequence encodes a polypeptide that binds and stimulates human VEGFR-2 and/or VEGFR-3. It is understood that variation in these exemplary conditions occur based on the length and GC nucleotide content of the sequences to be hybridized. Formulas standard in the art are appropriate for determining appropriate hybridization conditions. See Sambrook et al., *Molecular Cloning: A Laboratory Manual* (Second ed., Cold Spring Harbor Laboratory Press, 1989) §§ 9.47-9.51.

In preferred embodiments, the VEGF-C polynucleotide further comprises additional sequences to facilitate the VEGF-C gene therapy. In one embodiment, a "naked" VEGF-C transgene (i.e., a transgene without a viral, liposomal, or other vector to facilitate transfection) is employed for gene therapy. In this embodiment, the VEGF-C polynucleotide preferably comprises a suitable promoter and/or enhancer sequence (e.g., cytomegalovirus promoter/enhancer [Lehner et al., *J. Clin. Microbiol.*, 29:2494-2502 (1991); Boshart et al., *Cell*, 41:521-530 (1985)]; Rous sarcoma virus promoter [Davis et al., *Hum. Gene Ther.*, 4:151 (1993)]; Tie promoter [Korhonen et al., *Blood*, 86(5): 1828-1835 (1995)]; or simian virus 40 promoter) for expression in the target mammalian cells, the promoter being operatively linked upstream (i.e., 5') of the VEGF-C coding sequence. The VEGF-C polynucleotide also preferably further includes a suitable polyadenylation sequence (e.g., the SV40 or human growth hormone gene polyadenylation sequence) operably linked downstream (i.e., 3') of the VEGF-C coding sequence. The polynucleotide may further optionally comprise sequences whose only intended function is to facilitate large-scale production of the vector, e.g., in bacteria, such as a bacterial origin of replication and a sequence encoding a selectable marker. However, in a preferred embodiment, such extraneous sequences are at least partially cleaved off prior to administration to humans according to methods of the invention. One can manufacture and administer such polynucleotides to achieve successful gene therapy using procedures that have been described in the literature for other transgenes. See, e.g., Isner et al., *Circulation*, 91: 2687-2692 (1995); and Isner et al., *Human Gene Therapy*, 7: 989-1011 (1996); incorporated herein by reference in the entirety.

Any suitable vector may be used to introduce the VEGF-C transgene into the host. Exemplary vectors that have been described in the literature include replication-deficient retroviral vectors, including but not limited to lentivirus vectors [Kim et al., *J. Virol.*, 72(1): 811-816 (1998); Kingsman & Johnson, *Scrip Magazine*, October, 1998, pp. 43-46.]; adeno-associated viral vectors [Gnatenko et al., *J. Investig. Med.*, 45: 87-98 (1997)]; adenoviral vectors [See, e.g., U.S. Pat. No. 5,792,453; Quantin et al., *Proc. Natl. Acad. Sci. USA*, 89: 2581-2584 (1992); Stratford-Perricadet et al., *J. Clin. Invest.*, 90: 626-630 (1992); and Rosenfeld et al., *Cell*, 68: 143-155 (1992)]; Lipofectin-mediated gene transfer (BRL); liposomal vectors [See, e.g., U.S. Pat. No. 5,631,237 (Liposomes comprising Sendai virus proteins)]; and combinations thereof. All of the foregoing documents are incorporated herein by reference in the entirety. Replication-deficient adenoviral vectors constitute a preferred embodiment.

In embodiments employing a viral vector, preferred polynucleotides still include a suitable promoter and polyadenylation sequence as described above. Moreover, it will be readily apparent that, in these embodiments, the polynucleotide further includes vector polynucleotide sequences (e.g., adenoviral polynucleotide sequences) operably connected to the sequence encoding a VEGF-C polypeptide.

Thus, in one embodiment the composition to be administered comprises a vector, wherein the vector comprises the VEGF-C polynucleotide. In a preferred embodiment, the vector is an adenovirus vector. In a highly preferred embodiment, the adenovirus vector is replication-deficient, i.e., it cannot replicate in the mammalian subject due to deletion of essential viral-replication sequences from the adenoviral genome. For example, the inventors contemplate a method wherein the vector comprises a replication-deficient adenovirus, the adenovirus comprising the VEGF-C polynucleotide operably connected to a promoter and flanked on either end by adenoviral polynucleotide sequences.

The composition to be administered according to methods of the invention preferably comprises (in addition to the polynucleotide or vector) a pharmaceutically-acceptable carrier solution such as water, saline, phosphate-buffered saline, glucose, or other carriers conventionally used to deliver therapeutics intravascularly. Multi-gene therapy is also contemplated, in which case the composition optionally comprises both the VEGF-C polynucleotide/vector and another polynucleotide/vector selected to prevent restenosis. Exemplary candidate genes/vectors for co-transfection with VEGF-C transgenes are described in the literature cited above, including genes encoding cytotoxic factors, cytostatic factors, endothelial growth factors, and smooth muscle cell growth/migration inhibitors. As described in greater detail below, a VEGF-D transgene is a preferred candidate for co-administration with the VEGF-C transgene. Co-administration of a VEGF transgene also is specifically contemplated.

The "administering" that is performed according to the present method may be performed using any medically-accepted means for introducing a therapeutic directly or indirectly into the vasculature of a mammalian subject, including but not limited to injections; oral ingestion; intranasal or topical administration; and the like. In a preferred embodiment, administration of the composition comprising the VEGF-C polynucleotide is performed intravascularly, such as by intravenous, intra-arterial, or intracoronary arterial injection.

In a highly preferred embodiment, the composition is administered locally, e.g., to the site of angioplasty or bypass. For example, the administering comprises a catheter-mediated transfer of the transgene-containing composition into a blood vessel of the mammalian subject, especially into a coronary artery of the mammalian subject. Exemplary materials and methods for local delivery are reviewed in Lincoff et al., *Circulation*, 90: 2070-2084 (1994); and Wilensky et al., *Trends Cardiovasc. Med.*, 3:163-170 (1993), both incorporated herein by reference. For example, the composition is administered using infusion-perfusion balloon catheters (preferably mircroporous balloon catheters) such as those that have been described in the literature for intracoronary drug infusions. See, e.g., U.S. Pat. No. 5,713,860 (Intravascular Catheter with Infusion Array); U.S. Pat. No. 5,087,244; U.S. Pat. No. 5,653,689; and Wolinsky et al., *J. Am. Coll. Cardiol.*, 15: 475-481 (1990) (Wolinsky Infusion Catheter); and Lambert et al., *Coron. Artery Dis.*, 4: 469-475 (1993), all of which are incorporated herein by reference in their entirety. Use of such catheters for site-directed somatic cell gene therapy is described, e.g., in Mazur et al., *Texas Heart Institute Journal*, 21; 104-111 (1994), incorporated herein by reference. In an embodiment where the VEGF-C transgene is administered in an adenovirus vector, the vector is preferably administered in a pharmaceutically acceptable carrier at a titer of $10^7$-$10^{13}$ viral particles, and more preferably at a titer of $10^9$-$10^{11}$ viral particles. The adenoviral vector composition preferably is infused over a period of 15 seconds to 30 minutes, more preferably 1 to 10 minutes.

For example, in patients with angina pectoris due to a single or multiple lesions in coronary arteries and for whom PTCA is prescribed on the basis of primary coronary angiogram findings, an exemplary protocol involves performing PTCA through a 7 F guiding catheter according to standard clinical practice using the femoral approach. If an optimal result is not achieved with PTCA alone, then an endovascular stent also is implanted. (A nonoptimal result is defined as residual stenosis of >30% of the luminal diameter according to a visual estimate, and B or C type dissection.) Arterial gene transfer at the site of balloon dilatation is performed with a replication-deficient adenoviral VEGF-C vector immediately after the angioplasty, but before stent implantation, using an infusion-perfusion balloon catheter. The size of the catheter will be selected to match the diameter of the artery as measured from the angiogram, varying, e.g., from 3.0 to 3.5 F in diameter. The balloon is inflated to the optimal pressure and gene transfer is performed during a 10 minute infusion at the rate of 0.5 ml/min with virus titer of $1.15 \times 10^{10}$.

In another embodiment, intravascular administration with a gel-coated catheter is contemplated, as has been described in the literature to introduce other transgenes. See, e.g., U.S. Pat. No. 5,674,192 (Catheter coated with tenaciously-adhered swellable hydrogel polymer); Riessen et al., *Human Gene Therapy*, 4: 749-758 (1993); and Steg et al., *Circulation*, 96: 408-411 (1997) and 90: 1648-1656 (1994); all incorporated herein by reference. Briefly, DNA in solution (e.g., the VEGF-C polynucleotide) is applied one or more times ex vivo to the surface of an inflated angioplasty catheter balloon coated with a hydrogel polymer (e.g., Slider with Hydroplus, Mansfield Boston Scientific Corp., Watertown, Mass.). The Hydroplus coating is a hydrophilic polyacrylic acid polymer that is cross-linked to the balloon to form a high molecular weight hydrogel tightly adhered to the balloon. The DNA covered hydrogel is permitted to dry before deflating the balloon. Re-inflation of the balloon intravascularly, during an angioplasty procedure, causes the transfer of the DNA to the vessel wall.

In yet another embodiment, an expandable elastic membrane or similar structure mounted to or integral with a balloon angioplasty catheter or stent is employed to deliver the VEGF-C transgene. See, e.g., U.S. Pat. Nos. 5,707,385, 5,697,967, 5,700,286, 5,800,507, and 5,776,184, all incorporated by reference herein.

In another variation, the composition containing the VEGF-C transgene is administered extravascularly, e.g., using a device to surround or encapsulate a portion of vessel. See, e.g., International Patent Publication WO 98/20027, incorporated herein by reference, describing a collar that is placed around the outside of an artery (e.g., during a bypass procedure) to deliver a transgene to the arterial wall via a plasmid or liposome vector.

In still another variation, endothelial cells or endothelial progenitor cells are transfected ex vivo with the VEGF-C transgene, and the transfected cells as administered to the mammalian subject. Exemplary procedures for seeding a vascular graft with genetically modified endothelial cells are described in U.S. Pat. No. 5,785,965, incorporated herein by reference.

If the mammalian subject is receiving a vascular graft, the VEGF-C transgene-containing composition may be directly applied to the isolated vessel segment prior to its being grafted in vivo.

In another aspect, the invention provides a method of treating a mammalian subject to prevent stenosis or restenosis of a blood vessel, comprising the step of administering to a mammalian subject in need of treatment to prevent stenosis or restenosis of a blood vessel a composition comprising a VEGF-C polypeptide, in an amount effective to prevent stenosis or restenosis of the blood vessel. In a preferred embodiment, the administering comprises implanting an intravascular stent in the mammalian subject, where the stent is coated or impregnated with the composition. Exemplary materials for constructing a drug-coated or drug-impregnated stent are described in literature cited above and reviewed in Lincoff et al., *Circulation*, 90: 2070-2084 (1994). In another preferred embodiment, the composition comprises microparticles composed of biodegradable polymers such as PGLA, non-degradable polymers, or biological polymers (e.g., starch) which particles encapsulate or are impregnated by the VEGF-C polypeptide. Such particles are delivered to the intravascular wall using, e.g., an infusion angioplasty catheter. Other techniques for achieving locally sustained drug delivery are reviewed in Wilensky et al., *Trends Caridovasc. Med.*, 3:163-170 (1993), incorporated herein by reference.

Administration via one or more intravenous injections subsequent to the angioplasty or bypass procedure also is contemplated. Localization of the VEGF-C polypeptides to the site of the procedure occurs due to expression of VEGF-C receptors on proliferating endothelial cells. Localization is further facilitated by recombinantly expressing the VEGF-C as a fusion polypeptide (e.g., fused to an apolipoprotein B-100 oligopeptide as described in Shih et al., *Proc. Nat'l. Acad. Sci. USA*, 87:1436-1440 (1990). Co-administration of VEGF-C polynucleotides and VEGF-C polypeptides also is contemplated.

In yet another embodiment, the invention provides the use of a VEGF-C polynucleotide or VEGF-C polypeptide for the manufacture of a medicament for the treatment or prevention of stenosis or restenosis of a blood vessel.

In still another embodiment, the invention provides a method of treating a mammalian subject to prevent stenosis or restenosis of a blood vessel, comprising the step of administering to a mammalian subject in need of treatment to prevent stenosis or restenosis of a blood vessel a composition comprising a polynucleotide, the polynucleotide comprising a nucleotide sequence that encodes a vascular endothelial growth factor D (VEGF-D) polypeptide. Such methods are practiced essentially as described herein with respect to VEGF-C-encoding polynucleotides, except that polynucleotides encoding VEGF-D are employed. A detailed description of the human VEGF-D gene and protein are provided in Achen, et al., *Proc. Nat'l Acad. Sci. U.S.A.*, 95(2): 548-553 (1998); International Patent Publication No. WO 98/07832, published Feb. 26, 1998; and in Genbank Accession No. AJ000185, all incorporated herein by reference. A cDNA and deduced amino acid sequence for prepro-VEGF-D is set forth herein in SEQ ID NOs: 3 and 4. Of course, due to the well-known degeneracy of the genetic code, there exist multiple VEGF-D encoding polynucleotide sequences, any of which may be employed according to the methods taught herein.

As described herein in detail with respect to VEGF-C, the use of polynucleotides that encode VEGF-D fragments, VEGF-D analogs, VEGF-D allelic and interspecies variants, and the like which possess in vivo anti-restenosis effects of human VEGF-D are all contemplated as being encompassed by the present invention.

In yet another embodiment, the invention provides a method of treating a mammalian subject to prevent stenosis or restenosis of a blood vessel, comprising the step of administering to a mammalian subject in need of treatment to prevent stenosis or restenosis of a blood vessel a composition comprising a VEGF-D polypeptide, in an amount effective to prevent stenosis or restenosis of the blood vessel. Such methods are practiced essentially as described herein with respect to VEGF-C polypeptides.

In a related aspect, the invention provides materials and devices for practice of the above-described methods.

For example, the polynucleotides, polypeptides, vectors, compositions, and the like that are described for use in methods of the invention are themselves intended as aspects of the invention.

Likewise, the invention also provides surgical devices that are used to treat circulatory disorders, such as intravascular (endovascular) stents, balloon catheters, infusion-perfusion catheters, extravascular collars, elastomeric membranes, and the like, which have been improved by coating with, impregnating with, adhering to, or encapsulating within the device a composition comprising a VEGF-C polynucleotide, a VEGF-C polypeptide, a VEGF-D polynucleotide, and/or a VEGF-D polypeptide.

For example, in one embodiment, the invention provides an endovascular stent characterized by an improvement wherein the stent is coated or impregnated with a composition, the comprising at least one anti-restenosis agent selected from the group consisting of VEGF-C polynucleotides, VEGF-C polypeptides, VEGF-D polynucleotides, and VEGF-D polypeptides. Exemplary stents that may be improved in this manner are described and depicted in U.S. Pat. Nos. 5,800,507 and 5,697,967 (Medtronic, Inc., describing an intraluminal stent comprising fibrin and an elutable drug capable of providing a treatment of restenosis); U.S. Pat. No. 5,776,184 (Medtronic, Inc., describing a stent with a porous coating comprising a polymer and a therapeutic substance in a solid or solid/solution with the polymer); U.S. Pat. No. 5,799,384 (Medtronic, Inc., describing a flexible, cylindrical, metal stent having a biocompatible polymeric surface to contact a body lumen); U.S. Pat. Nos. 5,824,048 and 5,679,400; and U.S. Pat. No. 5,779,729; all of which are specifically incorporated herein by reference in the entirety. Implantation of such stents during conventional angioplasty techniques will result in less restenosis than implantation of conventional stents. In this sense, the biocompatibility of the stent is improved.

In another embodiment, the invention provides an extravascular collar for delivery of a therapeutic agent to a blood vessel, characterized by an improvement wherein the collar is coated with or impregnated with or encapsulates a composition, the comprising at least one anti-restenosis agent selected from the group consisting of VEGF-C polynucleotides, VEGF-C polypeptides, VEGF-D polynucleotides, and VEGF-D polypeptides. An exemplary collar to be improved in this manner is described and depicted in International Patent Publication WO 98/20027 (Eurogene, Ltd., collar comprising a body adopted to provide a seal around a vessel and to define a reservoir for holding an anti-restenosis pharmaceutical formulation), incorporated herein by reference.

In yet another embodiment, the invention provides a polymer film for wrapping a stent, characterized by an improvement wherein the film is coated with or impregnated with a composition, the comprising at least one anti-restenosis agent selected from the group consisting of VEGF-C polynucleotides, VEGF-C polypeptides, VEGF-D polynucleotides, and VEGF-D polypeptides. An exemplary film to be improved in this manner is described and depicted in U.S. Pat. Nos. 5,700,286 and 5,707,385 (Advanced Cardiovascular Systems, Inc., sheaths of bioabsorbable polymeric material coated or impregnated with a restenosis-preventing therapeutic agent and attachable to an endovascular stent).

Similarly, the invention includes kits which comprise compounds or compositions of the invention packaged in a manner which facilitates their use to practice methods of the invention. In a simplest embodiment, such a kit includes a compound or composition described herein as useful for practice of the invention (e.g., VEGF-C or VEGF-D polynucleotides or polypeptides), packaged in a container such as a sealed bottle or vessel, with a label affixed to the container or included in the package that describes use of the compound or composition to practice the method of the invention. Preferably, the compound or composition is packaged in a unit dosage form. In another embodiment, a kit of the invention includes both a VEGF-C or VEGF-D polynucleotide or polypeptide composition packaged together with a physical device useful for implementing methods of the invention, such as a stent, a catheter, an extravascular collar, a polymer film, or the like. In another embodiment, a kit of the invention includes both a VEGF-C or VEGF-D polynucleotide or polypeptide composition packaged together with a hydrogel polymer, or microparticle polymers, or other carriers described herein as useful for delivery of the VEGF-C/VEGF-D to the patient.

Additional features and variations of the invention will be apparent to those skilled in the art from the entirety of this application, and all such features are intended as aspects of the invention.

Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION OF THE INVENTION

Figure 1:
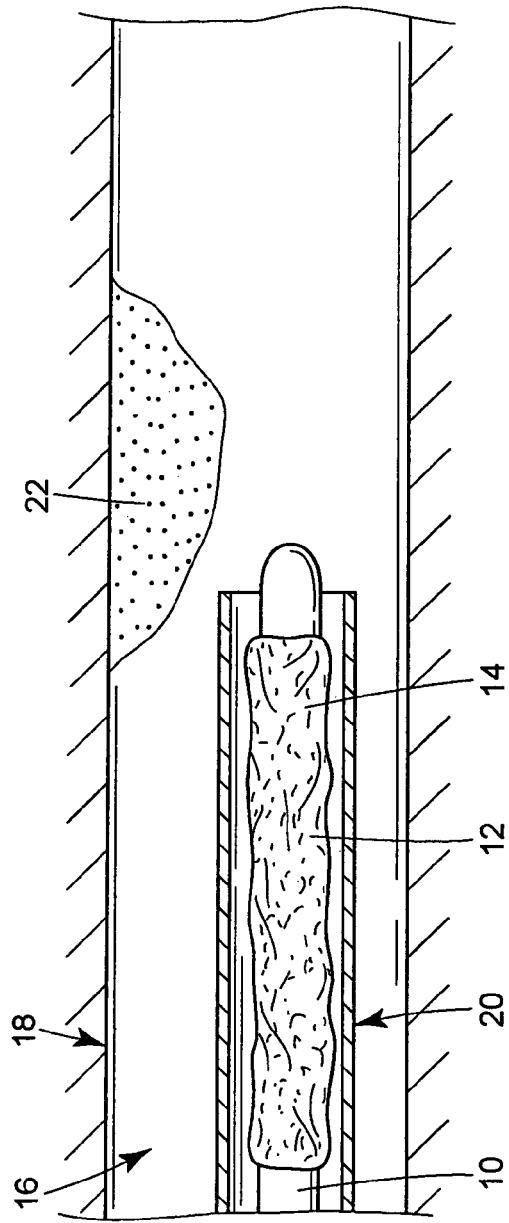
FIG. 1 depicts a cross-section of a blood vessel into which a drug delivery balloon catheter including a protective sheath has been inserted, the protective sheath serving to cover the balloon during insertion and positioning.

The present invention is based on the discovery that when a gene encoding human Vascular Endothelial Growth Factor C (VEGF-C) is administered to a mammal that has suffered a vascular trauma, such as the trauma that can occur during conventional balloon angioplasty procedures, restenosis of the injured vessel is reduced or eliminated. An in vivo controlled experiment demonstrating the efficacy of a VEGF-C transgene to prevent restenosis is described in detail in Example 1. Example 2 provides a side-by-side comparative study demonstrating that the anti-restenosis effects of VEGF-C appear superior to the anti-restenosis effects of VEGF administered in a comparable manner.

The growth factor named Vascular Endothelial Growth Factor C (VEGF-C), as well as native human, non-human mammalian, and avian polynucleotide sequences encoding VEGF-C, and VEGF-C variants and analogs, have been described in detail in International Patent Application Number PCT/US98/01973, filed Feb. 2, 1998 and published on 6 Aug. 1998 as International Publication Number WO 98/33917; in Joukov et al., J. Biol. Chem., 273(12): 6599-6602 (1998); and in Joukov et al., EMBO J., 16(13): 3898-3911 (1997), all of which are incorporated herein by reference in the entirety. As explained therein in detail, human VEGF-C is initially produced in human cells as a prepro-VEGF-C polypeptide of 419 amino acids. A cDNA and deduced amino acid sequence for human prepro-VEGF-C are set forth in SEQ ID NOs: 1 and 2, respectively, and a cDNA encoding human VEGF-C has been deposited with the American Type Culture Collection (ATCC), 10801 University Blvd., Manassas, Va. 20110-2209 (USA), pursuant to the provisions of the Budapest Treaty (Deposit date of 24 Jul. 1995 and ATCC Accession Number 97231). VEGF-C sequences from other species also have been reported. See Genbank Accession Nos. MMU73620 (Mus musculus); and CCY15837 (Coturnix coturnix) for example, incorporated herein by reference.

The prepro-VEGF-C polypeptide is processed in multiple stages to produce a mature and most active VEGF-C polypeptide of about 21-23 kD (as assessed by SDS-PAGE under reducing conditions). Such processing includes cleavage of a signal peptide (SEQ ID NO: 2, residues 1-31); cleavage of a carboxyl-terminal peptide (corresponding approximately to amino acids 228-419 of SEQ ID NO: 2 and having a pattern of spaced cysteine residues reminiscent of a Balbiani ring 3 protein (BR3P) sequence [Dignam et al., Gene, 88:133-40 (1990); Paulsson et al., J. Mol. Biol., 211:331-49 (1990)]) to produce a partially-processed form of about 29 kD; and cleavage (apparently extracellularly) of an amino-terminal peptide (corresponding approximately to amino acids 32-103 of SEQ ID NO: 2) to produced a fully-processed mature form of about 21-23 kD. Experimental evidence demonstrates that partially-processed forms of VEGF-C (e.g., the 29 kD form) are able to bind the Flt4 (VEGFR-3) receptor, whereas high affinity binding to VEGFR-2 occurs only with the fully processed forms of VEGF-C. It appears that VEGF-C polypeptides naturally associate as non-disulfide linked dimers.

Moreover, it has been demonstrated that amino acids 103-227 of SEQ ID NO: 2 are not all critical for maintaining VEGF-C functions. A polypeptide consisting of amino acids 113-213 (and lacking residues 103-112 and 214-227) of SEQ ID NO: 2 retains the ability to bind and stimulate VEGF-C receptors, and it is expected that a polypeptide spanning from about residue 131 to about residue 211 will retain VEGF-C biological activity. The cysteine residue at position 156 has been shown to be important for VEGFR-2 binding ability. However, VEGF-C $\Delta C_{156}$ polypeptides (i.e., analogs that lack this cysteine due to deletion or substitution) remain potent activators of VEGFR-3. If the anti-restenosis effects of VEGF-C are mediated through VEGFR-3, then use of VEGF-C $\Delta C_{156}$ polypeptides (and polynucleotides encoding them) is expected to provide anti-restenosis efficacy while minimizing VEGFR-2-mediated side-effects. The cysteine at position 165 of SEQ ID NO: 2 is essential for binding either receptor, whereas analogs lacking the cysteines at positions 83 or 137 compete with native VEGF-C for binding with both receptors and stimulate both receptors.

An alignment of human VEGF-C with VEGF-C from other species (performed using any generally accepted alignment algorithm) suggests additional residues wherein modifications can be introduced (e.g., insertions, substitutions, and/or deletions) without destroying VEGF-C biological activity. Any position at which aligned VEGF-C polypeptides of two or more species have different amino acids, especially different amino acids with side chains of different chemical character, is a likely position susceptible to modification without concomitant elimination of function. An exemplary alignment of human, murine, and quail VEGF-C is set forth in FIG. 5 of PCT/US98/01973.

Apart from the foregoing considerations, it will be understood that innumerable conservative amino acid substitutions can be performed to a wildtype VEGF-C sequence which are likely to result in a polypeptide that retains VEGF-C biological activities, especially if the number of such substitutions is small. By "conservative amino acid substitution" is meant substitution of an amino acid with an amino acid having a side chain of a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine). Addition or deletion of one or a few internal amino acids without destroying VEGF-C biological activities also is contemplated.

Without intending to be limited to a particular theory, the mechanism behind the efficacy of VEGF-C in preventing restenosis is believed to relate to the ability of VEGF-C to stimulate re-endothelialization of the injured vessel (and/or of the intravascular stent) without significant concomitant stimulation of smooth muscle proliferation in the vessel. VEGF-C also may inhibit smooth muscle cell proliferation. Accordingly, candidate VEGF-C analog polypeptides can be rapidly screened first for their ability to bind and stimulate autophosphorylation of known VEGF-C receptors (VEGFR-2 and VEGFR-3). Polypeptides that stimulate one or both known receptors are rapidly re-screened in vitro for their mitogenic and/or chemotactic activity against cultured capillary or arterial endothelial cells (e.g., as described in WO 98/33917). Polypeptides with mitogenic and/or chemotactic activity are then screened in vivo as described herein for the ability to prevent restenosis. In this way, variants (analogs) of naturally occurring VEGF-C proteins are rapidly screened to determine whether or not the variants have the requisite biological activity to constitute "VEGF-C polypeptides" for use in the present invention.

The growth factor named Vascular Endothelial Growth Factor D (VEGF-D), as well as human sequences encoding VEGF-D, and VEGF-D variants and analogs, have been described in detail in International Patent Application Number PCT/US97/14696, filed 21 Aug. 1997 and published on 26 Feb. 1998 as International Publication Number WO 98/07832; and in Achen, et al., *Proc. Nat'l Acad. Sci. U.S.A.*, 95(2): 548-553 (1998), both incorporated herein by reference in the entirety. As explained therein in detail, human VEGF-D is initially produced in human cells as a prepro-VEGF-D polypeptide of 354 amino acids. A cDNA and deduced amino acid sequence for human prepro-VEGF-D are set forth in SEQ ID NOs: 3 and 4, respectively. VEGF-D sequences from other species also have been reported. See Genbank Accession Nos. D89628 (Mus musculus); and AF014827 (Rattus norvegicus), for example, incorporated herein by reference.

The prepro-VEGF-D polypeptide has a putative signal peptide of 21 amino acids and is apparently proteolytically processed in a manner analogous to the processing of prepro-VEGF-C. A "recombinantly matured" VEGF-D lacking residues 1-92 and 202-354 of SEQ ID NO: 4 retains the ability to activate receptors VEGFR-2 and VEGFR-3, and appears to associate as non-covalently linked dimers. Thus, preferred VEGF-D polynucleotides include those polynucleotides that comprise a nucleotide sequence encoding amino acids 93-201 of SEQ ID NO: 4. The guidance provided above for introducing function-preserving modifications into VEGF-C polypeptides is also suitable for introducing function-preserving modifications into VEGF-D polypeptides.

A therapeutic or prophylactic treatment of restenosis provided by the present invention involves administering to a mammalian subjection such as a human a composition comprising a VEGF-C or VEGF-D polynucleotide or polypeptide or combination thereof (sometimes generically referred to herein as a "VEGF-C or VEGF-D therapeutic agent").

The "administering" may be performed using any medically-accepted means for introducing a therapeutic directly or indirectly into the vasculature of a mammalian subject, including but not limited to injections; oral ingestion; intranasal or topical administration; and the like. In a preferred embodiment, administration of the composition comprising the VEGF-C or VEGF-D polynucleotide or polypeptide composition is performed intravascularly, such as by intravenous, intra-arterial, or intracoronary arterial injection.

In a highly preferred embodiment, the composition is administered locally, e.g., to the site of angioplasty or bypass. For example, the administering comprises a catheter-mediated transfer of the therapeutic composition into a blood vessel of the mammalian subject, especially into a coronary artery of the mammalian subject. Exemplary materials and methods for local delivery are reviewed in Lincoff et al., *Circulation*, 90: 2070-2084 (1994); and Wilensky et al., *Trends Cardiovasc. Med.*, 3:163-170 (1993), both incorporated herein by reference. For example, the composition is administered using infusion-perfusion balloon catheters (preferably mircroporous balloon catheters) such as those that have been described in the literature for intracoronary drug infusions. See, e.g., U.S. Pat. No. 5,713,860 (Intravascular Catheter with Infusion Array); U.S. Pat. No. 5,087,244; U.S. Pat. No. 5,653,689; and Wolinsky et al., *J. Am. Coll. Cardiol.*, 15: 475-481 (1990) (Wolinsky Infusion Catheter); and Lambert et al., *Coron. Artery Dis.*, 4: 469-475 (1993), all of which are incorporated herein by reference in their entirety. Use of such catheters for site-directed somatic cell gene therapy is described, e.g., in Mazur et al., *Texas Heart Institute Journal*, 21; 104-111 (1994), incorporated herein by reference.

For example, in patients with angina pectoris due to a single or multiple lesions in coronary arteries and for whom PTCA is prescribed on the basis of primary coronary angiogram findings, an exemplary protocol involves performing PTCA through a 7 F guiding catheter according to standard clinical practice using the femoral approach. If an optimal result is not achieved with PTCA alone, then an endovascular stent also is implanted. (A nonoptimal result is defined as residual stenosis of >30% of the luminal diameter according to a visual estimate, and B or C type dissection.) Arterial gene transfer at the site of balloon dilatation is performed immediately after the angioplasty, but before stent implantation, using an infusion-perfusion balloon catheter. The size of the catheter will be selected to match the diameter of the artery as measured from the angiogram, varying, e.g., from 3.0 to 3.5 F in diameter. The balloon is inflated to the optimal pressure and gene transfer is performed during a 10 minute infusion at the rate of 0.5 ml/min with virus titer of $1.15 \times 10^{10}$.

In another embodiment, intravascular administration with a gel-coated catheter is contemplated, as has been described in the literature to introduce other transgenes. See, e.g., U.S. Pat. No. 5,674,192 (Catheter coated with tenaciously-adhered swellable hydrogel polymer); Riessen et al., *Human Gene Therapy*, 4: 749-758 (1993); and Steg et al., *Circulation*, 96: 408-411 (1997) and 90: 1648-1656 (1994); all incorporated herein by reference. As shown in FIG. 1, a catheter 10 is provided to which an inflatable baloon 12 is attached at a distal end. The balloon includes a swellable hydrogel polymer coating 14 capable of absorbing a solution comprising a therapeutic VEGF-C or VEGF-D therapeutic agent. Briefly, DNA in solution (e.g., the VEGF-C or VEGF-D polynucleotide) is applied one or more times ex vivo to the surface of an inflated angioplasty catheter balloon coated with a hydrogel polymer (e.g., Slider with Hydroplus, Mansfield Boston Scientific Corp., Watertown, Mass.). The Hydroplus coating is a hydrophilic polyacrylic acid polymer that is cross-linked to the balloon to form a high molecular weight hydrogel tightly adhered to the balloon. The DNA covered hydrogel is permitted to dry before deflating the balloon. Re-inflation of the balloon intravascularly, during an angioplasty procedure, causes the transfer of the DNA to the vessel wall. Thus, referring again to FIG. 1, the catheter with attached, coated balloon is inserted into the lumen 16 of a blood vessel 18 while covered by a protective sheath 20 to minimize exposure of the coated balloon to the blood prior to placement at the site of an occlusion 22. When the instrument has been positioned at the treatment region, the protective sheath is drawn back or the catheter is moved forward to expose the balloon, which is inflated to compress the balloon (and thus the coating) into the vessel wall, causing transfer of the VEGF-C or VEGF-D therapeutic agent to the tissue, in a manner analogous to squeezing liquid from a compressed sponge or transferring wet paint to a surface by contact.

Figure 2A:
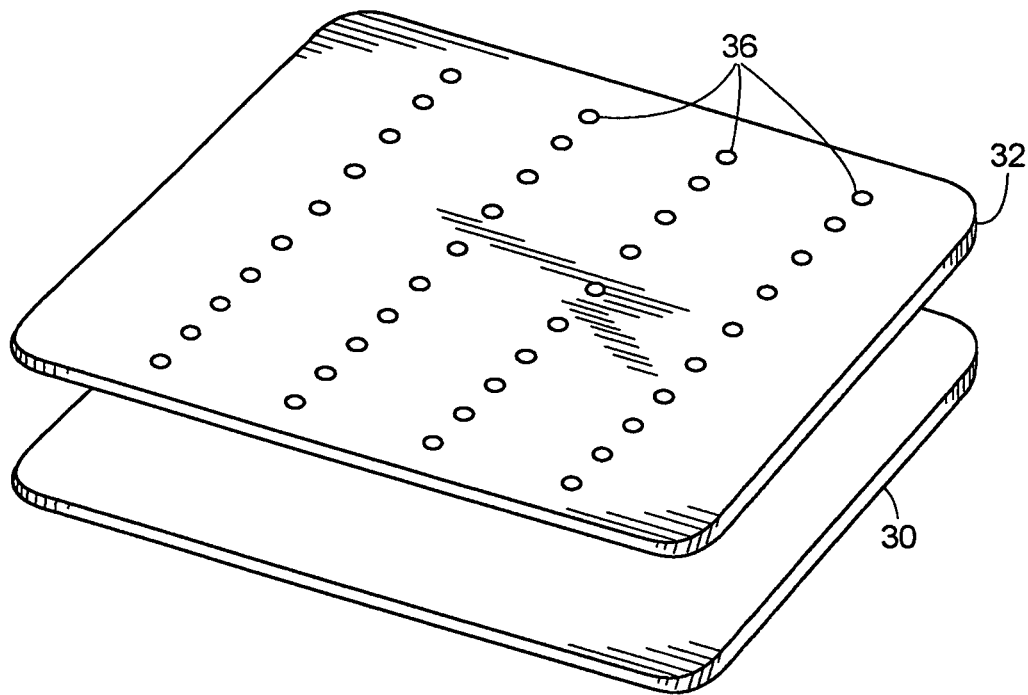
FIG. 2A depicts a perspective view of an expandable membrane having two layers that are spaced apart, prior to joining edges of the layers to each other.
Figure 2B:
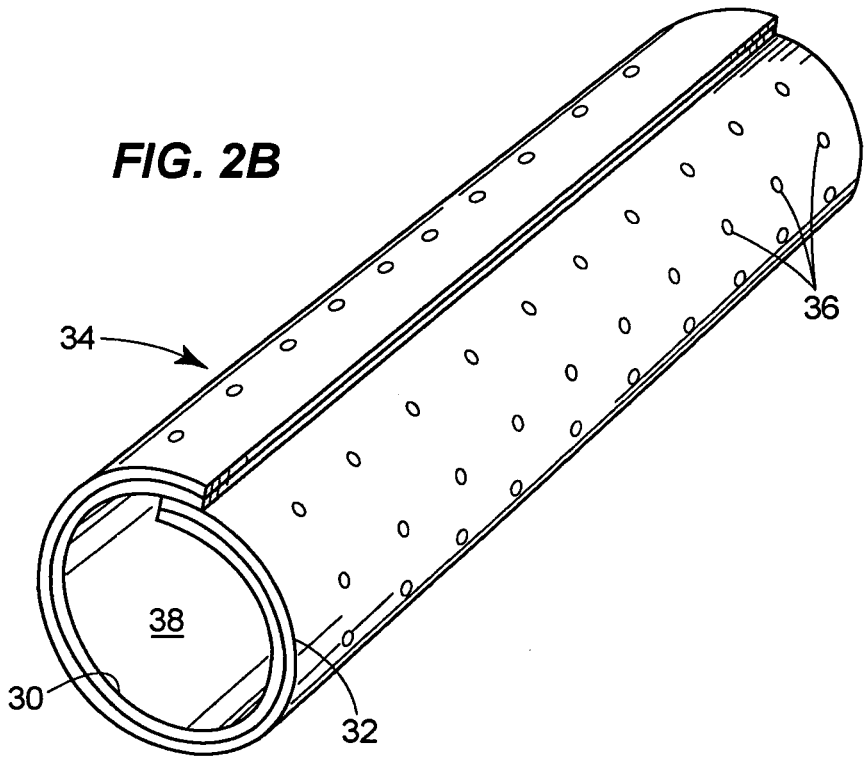
FIG. 2B depicts a perspective view of the membrane of FIG. 2A that has been rolled into a tube and had opposite edges adjoined.

In yet another embodiment, an expandable elastic membrane, film, or similar structure, mounted to or integral with a balloon angioplasty catheter or stent, is employed to deliver the VEGF-C or VEGF-D therapeutic agent. See, e.g., U.S. Pat. Nos. 5,707,385, 5,697,967, 5,700,286, 5,800,507, and 5,776,184, all incorporated by reference herein. As shown in FIGS. 2A-2B, a single layer 30 or multi-layer 30, 32 sheet of elastic membrane material (FIG. 2A) is formed into a tubular structure 34 (FIG. 2B), e.g., by bringing together and adhering opposite edges of the sheet(s), e.g., in an overlapping or a abutting relationship. In this manner the elastomeric material may be wrapped around a catheter balloon or stent. A therapeutic VEGF-C or VEGF-D composition is combined with the membrane using any suitable means, including injection molding, coating, diffusion, and absorption techniques. In the multilayer embodiment depicted in the Figures, the edges of the two layers may be joined to form a fluid-tight seal. In a preferred embodiment, one layer of material is first processed by stretching the material and introducing a plurality of microscopic holes or slits 36. After the layers have been joined together, the sheet can be stretched and injected with the therapeutic VEGF-C/D composition through one of the holes or slits to fill the cavity that exists between the layers. The sheet is then relaxed, causing the holes to close and sealing the therapeutic composition between the layers until such time as the sheet is again stretched. This occurs, for example, at the time that an endovascular stent or balloon covered by the sheet is expanded within the lumen of a stenosed blood vessel. The expanding stent or balloon presses radially outward against the inner surface 38 of the tubular sheet covering, thus stretching the sheet, opening the holes, and delivering the therapeutic agent to the walls of the vessel.

Figure 3A:
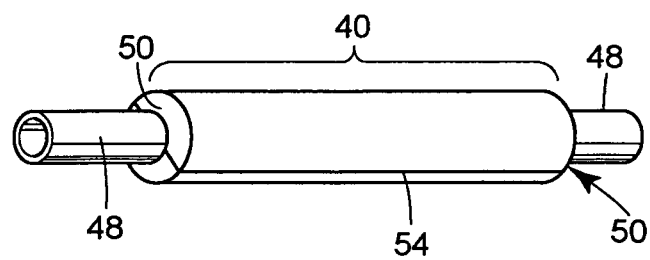
FIGS. 3A and 3B depict, in perspective (3A) and longitudinal cross-section (3B), schematic views of an extravascular collar surrounding a portion of a blood vessel.
Figure 3B:
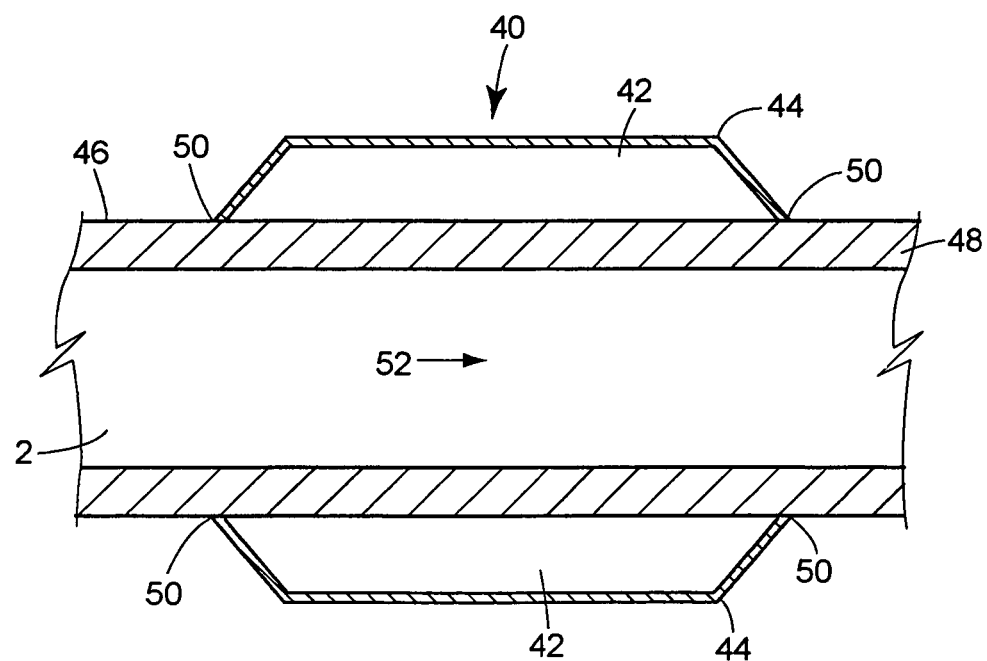

In another variation, the composition containing the VEGF-C or VEGF-D therapeutic is administered extravascularly, e.g., using a device to surround or encapsulate a portion of vessel. See, e.g., International Patent Publication WO 98/20027, incorporated herein by reference, describing a collar that is placed around the outside of an artery (e.g., during a bypass procedure) to deliver a transgene to the arterial wall via a plasmid or liposome vector. As shown in FIGS. 3A and 3B, an extravascular collar 40 including a void space 42 defined by a wall 44 formed, e.g., of a biodegradable or biocompatible material. The collar touches the outer wall 46 of a blood vessel 48 at the collar's outer extremities 50. Blood 52 flows through the lumen of the blood vessel. A longitudinal slit 54 in the flexible collar permits the collar to be deformed and placed around the vessel and then sealed using a conventional tissue glue, such as a thrombin glue.

In still another variation, endothelial cells or endothelial progenitor cells are transfected ex vivo with the VEGF-C a VEGF-D transgene, and the transfected cells as administered to the mammalian subject. Exemplary procedures for seeding a vascular graft with genetically modified endothelial cells are described in U.S. Pat. No. 5,785,965, incorporated herein by reference.

If the mammalian subject is receiving a vascular graft, the VEGF-C or VEGF-D therapeutic composition may be directly applied to the isolated vessel segment prior to its being grafted in vivo.

Figure 4B:
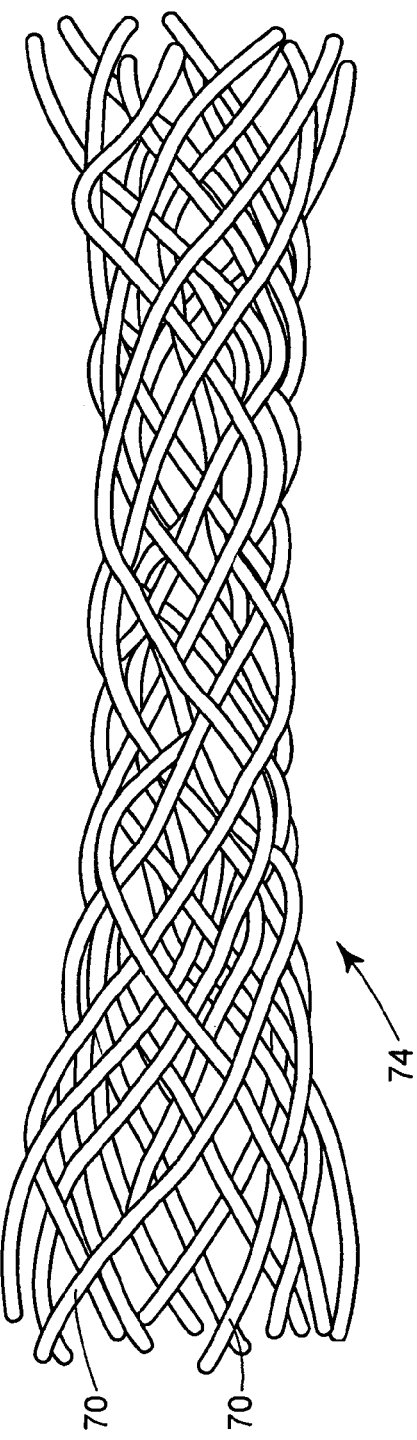
FIG. 4B depicts a perspective view of an intravascular stent formed from the wire of FIG. 4A.
Figure 4A:
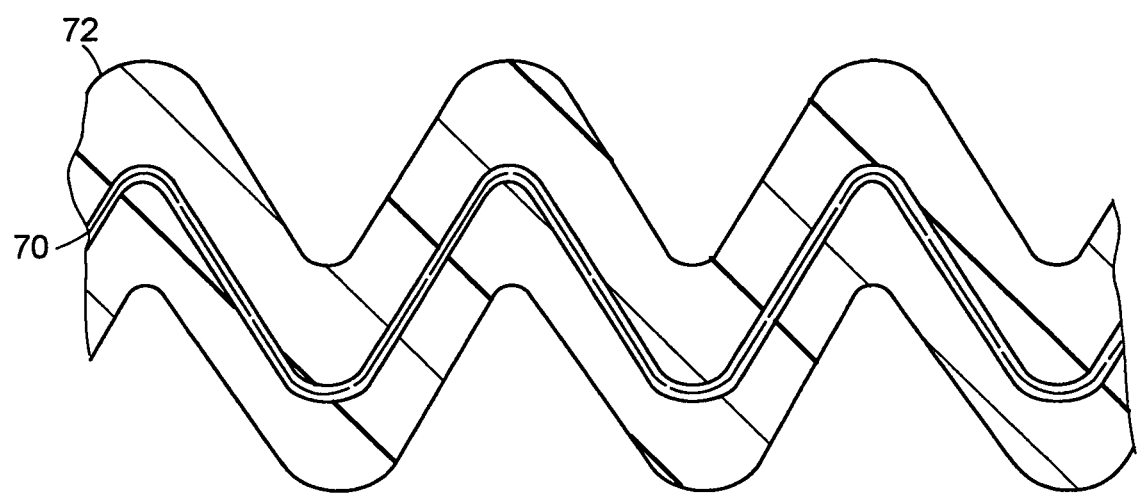
FIG. 4A depicts in cross-section a wire coated with a polymer or gel that can include (e.g., be impregnated with) a therapeutic composition.

In another preferred embodiment, the administering comprises implanting an intravascular stent in the mammalian subject, where the stent is coated or impregnated with the therapeutic VEGF-C/D gene/protein composition. Exemplary materials for constructing a drug-coated or drug-impregnated stent are described in literature cited above and reviewed in Lincoff et al., *Circulation*, 90: 2070-2084 (1994). As shown in FIGS. 4A and 4B, a metal or polymeric wire 70 for forming a stent is coated with a composition 72 such as a porous biocompatible polymer or gel that is impregnated with (or can be dipped in or otherwise easily coated immediately prior to use with) a VEGF-C or VEGF-D therapeutic composition. The wire is coiled, woven, or otherwise formed into a stent 74 suitable for implanation into the lumen of a vessel using conventional materials and techniques, such as intravascular angioplasty catheterization. Exemplary stents that may be improved in this manner are described and depicted in U.S. Pat. Nos. 5,800,507 and 5,697,967 (Medtronic, Inc., describing an intraluminal stent comprising fibrin and an elutable drug capable of providing a treatment of restenosis); U.S. Pat. No. 5,776,184 (Medtronic, Inc., describing a stent with a porous coating comprising a polymer and a therapeutic substance in a solid or solid/solution with the polymer); U.S. Pat. No. 5,799,384 (Medtronic, Inc., describing a flexible, cylindrical, metal stent having a biocompatible polymeric surface to contact a body lumen); U.S. Pat. Nos. 5,824,048 and 5,679,400; and U.S. Pat. No. 5,779,729; all of which are specifically incorporated herein by reference in the entirety. Implantation of such stents during conventional angioplasty techniques will result in less restenosis than implantation of conventional stents. In this sense, the biocompatibility of the stent is improved.

In another preferred embodiment, the composition comprises microparticles composed of biodegradable polymers such as PGLA, non-degradable polymers, or biological polymers (e.g., starch) which particles encapsulate or are impregnated by the VEGF-C or VEGF-C polypeptide/polynucleotide. Such particles are delivered to the intravascular wall using, e.g., an infusion angioplasty catheter. Other techniques for achieving locally sustained drug delivery are reviewed in Wilensky et al., *Trends Caridovasc. Med.*, 3:163-170 (1993), incorporated herein by reference.

Administration via one or more intravenous injections subsequent to the angioplasty or bypass procedure also is contemplated. Localization of the VEGF-C or VEGF-D polypeptides to the site of the procedure occurs due to expression of VEGF-C/D receptors on proliferating endothelial cells. Localization is further facilitated by recombinantly expressing the VEGF-C or VEGF-D as a fusion polypeptide (e.g., fused to an apolipoprotein B-100 oligopeptide as described in Shih et al., *Proc. Nat'l. Acad. Sci. USA*, 87:1436-1440 (1990).

The pharmaceutical efficacy of VEGF-C polynucleotides, VEGF-C polypeptides, VEGF-D polynucleotides, and VEGF-D polypeptides to prevent stenosis or restenosis of a blood vessel is demonstrated in vivo, e.g., using procedures such as those described in the following examples, some of which are prophetic. The examples assist in further describing the invention, but are not intended in any way to limit the scope of the invention.

EXAMPLE 1

Use of Adenovirus-Mediated VEGF-C Gene Transfer to Prevent Restenosis

The following experiments, performed in vivo in a rabbit restenosis model, demonstrate the efficacy of adenovirus-mediated intravascular VEGF-C gene transfer for the prevention of post-angioplasty restenosis.

A. Materials and Methods

1. Adenoviral Constructs.

An adenovirus plasmid containing a cDNA encoding the complete human prepro-VEGF-C open reading frame operably linked to a cytomegalovirus (CMV) promoter and human growth hormone polyadenylation signal sequence was constructed as follows. A DNA fragment comprising a CMV promoter sequence was prepared by digesting the pcDNA3.1+ vector (Invitrogen) with Sal I and filling-in the 5' overhangs with the Klenow enzyme. The CMV promoter (nucleotides 5431-911) was excised from the vector with Hind III and isolated. A full-length human VEGF-C cDNA containing the 1997 bp sequence specified in SEQ ID NO: 1 (as well as less than 50 bases of additional non-coding and polylinker sequence) was excised from a VEGF-C pREP7 expression vector [described in WO 98/33917] with Hind III and Xho I and isolated. A human growth hormone polyadenylation signal (~860 bp) was excised from an αMHC vector with SalI and BamHI. The CMV promoter, VEGF-C cDNA, and hGH polyadenylation signal fragments were simultaneously ligated into a BamHI and EcoRV-digested pCRII vector. The ligated CMV promoter and VEGF-C cDNA is shown in SEQ ID NO: 17. The resulting construct was opened with BglII and partially-digested with BamHI. The full transcriptional unit was ligated into BglII-opened pAdBg1II vector. This construct [designated pAdBg1II VEGF-C] was then used to create recombinant adenovirus containing the CMV-VEGF-C-hGH transcriptional unit, using standard homologous recombination techniques. [Barr et al., *Gene Ther.*, 1: 51-58 (1994).] Replication-deficient E1-E3 deleted adenoviruses were produced in 293 cells and concentrated by ultracentrifugation using techniques known in the literature. [See, e.g., Barr et al. (1994).] A control plasmid comprising the lacZ gene operably linked to the same promoter was also used. [Laitinen M. et al., *Hum. Gene Ther.*, 9: 1481-1486 (1998).] The lacZ adenovirus had a nuclear targeted signal, to direct the β-galactosidase expression to the nucleus. Replication-deficient E1-E3 deleted adenoviruses were produced in 293 cells and concentrated by ultracentrifugation (Barr et al., 1994). The adenoviral preparations were analyzed for the absence of helper viruses and bacteriological contaminants.

2. Animal Model.

New Zealand White rabbits were employed for the gene transfer study. A first group of rabbits was fed a 0.25% cholesterol diet for two weeks, then subjected to balloon denudation of the aorta, then subjected three days later to the adenovirus-mediated gene transfer. A second group of rabbits was only subjected to the gene transfer. Animals were sacrificed 2 or 4 weeks after the gene transfer. The number of experimental (VEGF-C) and control (lacZ) animals in both study groups was 6.

In the first group of rabbits, the whole aorta, beginning from the tip of the arch, was denuded using a 4.0 F arterial embolectomy catheter (Sorin Biomedical, Irvine, Calif.). The catheter was introduced via the right iliac artery up to the aortic arch and inflated, and the aorta was denuded twice.

3. Gene Transfer.

The gene transfer was performed using a 3.0 F channel balloon local drug delivery catheter (Boston Scientific Corp., Maple Grove, Mass.). Using fluoroscopical control, the balloon catheter was positioned caudal to the left renal artery, in a segment free of side branches, via a 5 F percutaneous introducer sheath (Arrow International, Reading, Pa.) in the right carotid artery and inflated to 6 ATM with a mixture of contrast media and saline. The anatomical location of the balloon catheter was determined by measuring its distance from the aortic orifice of the left renal artery. Virus titer of $1.15 \times 10^{10}$ plaque forming units (pfu) was administered to each animal in a final volume of 2 ml (0.9% NaCl), and the gene transfer was performed at 6 ATM pressure for 10 minutes (0.2 ml/min). In the second study group the animals had only gene transfer and they were sacrificed 2 weeks after the gene transfer. The number of animals in each study group (0.9% NaCl only; lacZ gene transfer; and VEGF-C gene transfer) was 3. All studies were approved by Experimental Animal Committee of the University of Kuopio in Finland.

4. Histology.

Three hours before sacrifice, the animals were injected intravenously with 50 mg of BrdU dissolved in 40% ethanol. After the sacrifice, the aortic segment where the gene transfer had been performed was removed, flushed gently with saline, and divided into five equal segments. The proximal segment was snap frozen in liquid nitrogen and stored at −70° C. The next segment was immersion-fixed in 4% paraformaldehyde/15% sucrose (pH 7.4) for 4 hours, rinsed in 15% sucrose (pH 7.4) overnight, and embedded in paraffin. The medial segment was immersion-fixed in 4% paraformaldehyde/phosphate buffered saline (PBS) (pH 7.4) for 10 minutes, rinsed 2 hours in PBS, embedded in OCT compound (Miles), and stored at −70° C. The fourth segment was immersion-fixed in 70% ethanol overnight and embedded in paraffin. The distal segment was directly stained for β-galactosidase activity in X-GAL staining solution at +37° C. for 16 hours, immersion-fixed in 4% paraformaldehyde/15% sucrose (pH 7.4) for 4 hours, rinsed in 15% sucrose overnight, and embedded in paraffin. Paraffin sections were used for immunocytochemical detection of smooth muscle cells (SMC), macrophages, and endothelium. Gene transfer efficiency was evaluated using X-GAL staining of OCT-embedded tissues. BrdU-positive cells were detected according to manufacturer's instructions. Morphometry was performed using haematoxylin-eosin stained paraffin sections using image analysis software. Measurements were taken independently by two observers from multiple sections, without knowledge of the origin of the sections. Intima/media (I/M) ratio was used as a parameter for intimal thickening.

B. Results.

Histological analysis of the balloon-denuded mice revealed that the lacz-transfected control group had an I/M ratio of 0.61 two weeks after the gene transfer, which represented a statistically significant difference ($p<0.05$) from the VEGF-C-transfected groups (I/M ratio of 0.40). The tendency that VEGF-C group had a smaller I/M ratio persisted at 4 weeks time point after the gene transfer.

In the second group of rabbits that were subjected only to gene transfer to the vessel wall (without endothelial denudation), the I/M ratio in the lacZ group was 0.3, compared to 0.15 for the VEGF-C group. This difference, too, represented a statistically significant ($p<0.05$) inhibition in neointima formation in VEGF-C group.

The BrdU labeling will permit analysis of smooth muscle cell proliferation in VEGF-C-transfected versus control (lacZ) animals. SMC proliferation is expected to be reduced in the VEGF-C-transfected population.

The foregoing data demonstrate that VEGF-C gene transfer significantly reduced intimal thickening at two weeks time point after aortic denudation and after vessel wall damage caused by the gene transfer catheter without balloon denudation. These data indicate a therapeutic utility for VEGF-C gene transfer for the prevention of post-angioplasty restenosis.

EXAMPLE 2

Comparative Example Demonstrating that Anti-Restenosis Effects of VEFG-C Appear Superior to Those of VEGF The following experiments demonstrate the efficacy of adenovirus-mediated intravascular VEGF and VEGF-C gene transfer for the prevention of post-angioplasty restenosis, and demonstrates that VEGF-C appeared to provide a superior therapeutic efficacy compared to VEGF.

A. Materials and Methods

1. Adenoviral Constructs.

VEGF (murine VEGF-$A_{164}$; SEQ ID NO: 18) adenovirus was constructed using the same promoter as the VEGF-C construct, and following similar procedure as described in Example 1. The VEGF-$A_{164}$ adenoviral construct was produced in 293T cells and concentrated essentially as described in Example 1, and analyzed to be free of helper virus, lipopolysaccharides, and bacterial contaminants.

2. Animal Model.

Sixty three New Zealand White rabbits were divided into two major groups, the first having 0.25% cholesterol diet for two weeks and balloon denudation of the aorta before gene transfer, and the second group having only the gene transfer. Gene transfer was performed in the first group of rabbits three days after denudation, and the animals were sacrificed 2 or 4 weeks after the gene transfer. Number of rabbits in each study group (lacZ, VEGF, and VEGF-C) at both time points was 6. In the second study group, the rabbits had only the gene transfer, without cholesterol diet or balloon denudation, and were sacrificed 2 or 4 weeks after the gene transfer. The number of rabbits in each study group (0.9% saline, lacZ, VEGF, and VEGF-C) was 3.

3. Gene Transfer.

Gene transfer was performed according to the procedure described in Example 1.

4. Histology

Histology was performed essentially as described in Example 1 with the following modifications: SMC were detected using HHF35 (DAKO, 1:50 dilution), macrophages were detected using RAM-11 (DAKO, 1:50 dilution), endothelium was detected using CD31 (DAKO, 1:50 dilution), and T cells were detected using MCA 805 (DAKO, 1:100 dilution). Controls for immunostainings included incubations with class-and species matched immunoglobulins and incubations where primary antibodies were omitted. Morphometry and image analysis were performed using Image-Pro Plus™ software and an Olympus AX70 microscope (Olympus Optical, Japan). Statistical analyses were performed using the ANOVA and modified t-test. $P<0.05$ was considered statistically significant.

B. Results

Histological analysis of the balloon-denuded rabbit aorta shows intimal thickening and SMC proliferation. Two weeks after gene transfer, the lacZ control group had the highest I/M ratio (0.57±0.04) whereas VEGF-C (0.38±0.02) and VEGF (0.49±0.17) groups showed decreased intimal thickening. The difference in I/M ratios between lacZ and VEGF-C groups was significant ($P<0.05$), whereas those between lacZ and VEGF groups were not statistically significant, at the two-week time point. The tendency that both VEGF and VEGF-C groups had smaller I/M ratios persisted at the four week time point when the I/M ratio was 0.73±0.16, 0.44±0.14, and 0.63±0.21 for the lacZ, VEGF-C, and VEGF groups, respectively. Hematoxylin-eosin and immunostainings of the transfected arteries indicate that intimal thickening in all arteries was composed predominantly of SMC.

Use of adenoviral vectors can lead to immnological and inflammatory responses, partly because high titer adenovirus induces expression of $NF_\kappa B$ and activates a CTL response. However, no signs of inflammation nor foam cell accumulation were detected as judged by macrophage and T-cell immunostainings. In addition, human clinical gene therapy grade viruses were used together with short exposure times in the transfected arteries, which may also help explain the absence of severe inflammatory reactions in this study.

The percentage of proliferating cells was analyzed using BrdU labeling. No significant differences were seen, although the VEGF-C group tended to have a lower proliferation rate, consistent with the observation that VEGF-C transduced arteries had smaller I/M ratios at both time points. Two weeks after balloon denudation, the percentage of proliferating cells was 1.8±0.4, 2.2±0.7, and 1.2±0.0 for the lacZ, VEGF, and VEGF-C groups, respectively, and after four weeks, the percentage of proliferating cells was 0.3±0.1, 1.2±0.5, and 0.3±0.1 for the lacZ, VEGF, and VEGF-C groups, respectively. Endothelial regrowth was analyzed by measuring the length of intact endothelium from histological sections. No significant differences were found between the study groups.

The potential of adenovirus to cause damage to the vessel wall and neointima formation was tested by performing hightiter adenovirus gene transfer to intact abdominal aorta of rabbits without balloon-denudation. Control rabbits were treated in the same way with 0.9% saline. The positioning of the gene transfer catheter caused some internal elastic lamina damage and moderate induction of neoinitma formation after the procedure. At the two-week time point, the I/M ratio in the lacZ group was 0.24±0.06, in the control group 0.28±0.05, in the VEGF-C group 0.18±0.07, and in the VEGF group 0.15±0.03. At the four-week time point the lacZ group had an I/M ratio of 0.22±0.13, the VEGF-C group 0.13±0.03, and the VEGF group 0.23±0.11.

This study shows a beneficial therapeutic effect of intravascular adenovirus-mediated VEGF-C gene transfer on the vessel wall after balloon injury, and also compares VEGF-C and VEGF adenovirus-mediated gene transfer for the prevention of neointima formation. Although different receptor binding profiles of VEGF-C and VEGF might have led to different biological effects in the vessel wall, both VEGFs reduced intimal thickening two weeks after gene transfer. Thus, both VEGFs are potential candidates for vascular gene therapy of ischemic atherosclerotic diseases. However, according to this experiment, VEGF-C appears to prevent restenosis more effectively than VEGF in this model system. The superior ability of VEGF-C to prevent restenosis, as compared to VEGF, could be due to expression or activity of VEGFR-3 which is a receptor for VEGF-C and VEGF-D, but not for VEGF. Alternatively, the apparent superiority may be attributable to a restenosis-promoting effect of VEGF mediated through VEGFR-1 or due to differential ligand effects (VEGF-C versus VEGF) mediated thru the common receptor VEGFR-2, which is reportedly expressed in vascular smooth muscle cells. [See Grosskreutz et al., *Microvasc. Res.*, 58(2): 128-136 (September, 1999).

EXAMPLE 3

Expression of Transfected VEGFs in the Aortic Wall

Using the aortic segments from the same experimental animals described in Example 2, mRNA expression of lacZ, VEGF-C and VEGF (murine VEGF-$A_{164}$) was analyzed in aortic tissue after gene transfer. Total RNA was extracted from transfected aortic segments using Trizol Reagent (Gibco-BRL), and 2 μg of RNA was used for cDNA synthesis. Primers for lacZ, VEGF-C and VEGF were designed to distinguish between endogenous and transduced genes by selecting the 5' primers from the CMV promoter and the 3' primers from the coding regions.

For lacZ amplification, primers were: 5' primer 5'-TTGGAGGCCTAGGCTTTTGC-3' (SEQ ID NO: 5) and 3' primer 5'-ATACTGTCGTCGTCCCCTCA-3' (SEQ ID NO: 6). The first PCR cycle was an initial incubation at 96° C. for 4 minutes followed by 80° C. for 3 minutes during which the DNA polymerase was added. This was followed by 30 cycles, each consisting of 94° C. for 45 seconds, 58° C. for 45 seconds, and 72° C. for 50 seconds, followed by a final extension of 72° C. for 5 minutes. 5 μl of the first PCR product was used for the second PCR with 5' primer 5'-GGTAGAAGACCCCAAGGACTTT-3'(SEQ ID NO: 7) and 3' primer 5'-CGCCATTCGCCATTCAG-3' (SEQ ID NO: 8). The first PCR cycle was an initial incubation at 96° C. for 3 minutes followed by 80° C. for 3 minutes followed by 32 cycles, each consisting of 94° C. for 60 seconds, 58° C. for 15 seconds, and 72° C. for 90 seconds, followed by a final extension of 72° C. for 5 minutes.

For VEGF-C amplification, primers were: 5' primer 5'-CTGCTTACTGGCTTATCG-3' (SEQ ID NO: 9) and 3' primer 5'-CCTGTTCTCTGTTATGTTGC-3' (SEQ ID NO: 10). The first PCR-cycle was an initial incubation at 96° C. for 4 minutes followed by 80° C. for 3 minutes during which the DNA polymerase was added. This was followed by 39 cycles each consisting of 94° C. for 30 seconds, 56° C. for 40 seconds, and 72° C. for 90 seconds, followed by a final extension of 72° C. for 5 minutes. 5 μl of the first PCR product was used for the second PCR with 5' primer 5'-TCTCCAAAAAGCTACACCG-3' (SEQ ID NO: 11) and 3' primer 5'-CAAGTGCATGGTGGAAGG-3' (SEQ ID NO: 12). The first PCR cycle was an initial incubation at 96° C. for 3 minutes followed by 80° C. for 3 minutes followed by 39 cycles each consisting of 94° C. for 60 seconds, 57° C. for 30 seconds, and 72° C. for 90 seconds, followed by a final extension of 72° C. for 5 minutes.

For VEGF amplification, primers were: 5' primer 5'-TCGATCCATGAACTTTCTGC-3' (SEQ ID NO: 13) and 3' primer 5'-TTCGTTTAACTCAAGCTGCC-3' (SEQ ID NO: 14). The first PCR cycle was an initial incubation at 96° C. for 4 minutes followed by 80° C. for 3 minutes, followed by 39 cycles each consisting of 94° C. for 30 seconds, 53° C. for 40 seconds, and 72° C. for 90 seconds, followed by a final extension of 72° C. for 5 minutes. 5 μl of the first PCR product was used for the second PCR with 5' primer 5'-GACCCTGGCTTTACTGCTG-3' (SEQ ID NO: 15) and 3' primer 5'-GGAACATTTACACGTCTGCG-3' (SEQ ID NO: 16). The first PCR cycle was an initial incubation at 96° C. for 3 minutes followed by 80° C. for 3 minutes followed by 39 cycles each consisting of 94° C. for 60 seconds, 54° C. for 30 seconds, and 72° C. for 90 seconds, followed by a final extension of 72° C. for 5 minutes.

The mRNA of lacZ, VEGF-C and VEGF was detected in aortic wall tissue up to four weeks after gene transfer.

Gene transfer efficiency was evaluated by assaying lacZ expression, analyzed by X-Gal staining for β-galactosidase activity, in OCT embedded tissue sections. Transfection efficiency was 1.1%±0.5 and 0.3%±0.1, two and four weeks respectively, after intravascular catheter-mediated gene transfer.

EXAMPLE 4

Expression of VEGF Receptors in the Aortic Wall

Using the experimental animals described in Example 2, VEGFR-1, VEGFR-2, and VEGFR-3 expression in aortic tissue was analyzed by immunostainings and in situ hybridization. Immunohisochemistry was performed using clone sc-316 (Santa Cruz Biotechnology, 1:50 dilution) to detect VEGFR-1, clone sc-6251 (Santa Cruz Biotechnology, 1:500 dilution) to detect VEGFR-2, and clone sc-637 (Santa Cruz Biotechnology, 1:300 dilution) to detect VEGFR-3. Controls for immunostainings included incubations with class- and species matched immunoglobulins and incubations where primary antibodies were omitted. In situ hybridization of VEGF receptor mRNAs was carried out using $^{33}$P-UTP labeled riboprobes. Expression of all receptors was localized to endothelium. VEGFR-2 was also expressed in neointimal SMCs.

EXAMPLE 5

Use of Naked VEGF-C Transgene Therapy to Prevent Restenosis

The procedures described in Example 1 or 2 are repeated, with the following modifications. Instead of using an adenovirus vector for delivery of the VEGF-C transgene, a mammalian expression vector is constructed for direct gene transfer (of naked plasmid DNA). The VEGF-C coding sequence is operably linked to a suitable promoter, such as the CMV promoter, and preferably linked to a suitable polyadenylation sequence, such as the human growth hormone polyadenylation sequence. Exemplary VEGF-C vectors can be modeled from vectors that have been described in the literature to perform vector-free gene transfer for other growth factors, by substituting a VEGF-C coding sequence for a VEGF coding sequence. [See, e.g., Isner et al., *Circulation*, 91: 2687-2692 (1995); and Isner et al., *Human Gene Therapy*, 7: 989-1011 (1996), incorporated herein by reference.] vector. A similar construct comprising a lacZ gene is used as a control.

A Hydrogel-coated balloon catheter (Boston Scientific) is used to deliver the VEGF-C transgene essentially as described in Asahara et al., *Circulation*, 94: 3291-3302 (Dec. 15, 1996), incorporated herein by reference. Briefly, an angioplasty balloon is prepared ex vivo by advancing the deflated balloon completely through a teflon protective sheath (Boston Scientific). The balloon is inflated and a conventional pipette is used to apply the transgene construct (e.g., 50-5000 μg transgene DNA in a saline solution) to the Hydrogel polymer coating the external surface of the inflated balloon. After the transgene solution has dried, the balloon is deflated, withdrawn into the protective sheath, and re-inflated to minimize blood flow across the balloon surface until the balloon is properly positioned in the target artery.

Intima/media (I/M) ratio is again used as a parameter for intimal thickening. Reduced I/M ratio in animals treated with the VEGF-C transgene-coated balloon catheter is considered indicative of therapeutic efficacy. As described in Example 2, comparison of the therapeutic efficacy of VEGF-C gene transfer with other therapies, such as VEGF gene transfer, can be conducted in parallel.

EXAMPLE 6

Use of VEGF-C Gene Therapy to Prevent Restenosis Following Angioplasty with Stent The procedures described in the preceding examples are repeated with the modification that initial balloon angioplasty is accompanied by implantation of a coronary stent using conventional procedures. The VEGF-C transgene is delivered concurrently or immediately before or after stent implantation essentially as described in the preceding examples. Increased quantities (e.g., two-fold to ten-fold) of the transgene (compared to angioplasty without stent) and increased transfection time may be desirable, as described in Van Belle et al., *J. Am. Coll. Cardiol.*, 29:1371-1379 (May, 1997), incorporated by reference herein. Decreased neointimal thickening and/or decreased thrombotic occlusion in the VEGF-C gene-treated animals versus control animals treated with a marker gene is considered evidence of the efficacy of the VEGF-C gene therapy.

EXAMPLE 7

Use of an Extravascular Collar to Reduce Vascular Stenosis

An inert silicone collar such as described in International Patent Publication No. WO 98/20027 is surgically implanted around the carotid arteries of New Zealand White Rabbits. The collar acts as an irritation agent that will induce intimal thickening, and contains a reservoir suitable for local delivery of a VEGF-C transgene or protein pharmaceutical formulation. Gene transfer, using the VEGF-C adenovirus construct or control construct described in Example 1 is initiated five days later by injecting $10^8$-$10^{11}$ pfu into the collar. Animals are sacrificed 14 or 28 days later and histological examinations are performed as described in Example 1. Intima/media thickness ratio [Yla-Herttuala et al., *Arteriosclerosis*, 6: 230-236 (1986)] is used as an indicia of stenosis. Reduced I/M ratio in the VEGF-C-transfected rabbits, as compared to the lacZ control rabbits, indicates therapeutic efficacy of VEGF-C gene transfer for preventing arterial stenosis.

EXAMPLE 8

Use of VEGF-C Polypeptides to Reduce or Prevent Restenosis

The procedures described in Example 1 are repeated except, instead of treating the test animals with an adenovirus containing a VEGF-C transgene or lacZ control, the animals are treated with a composition comprising a VEGF-C polypeptide in a pharmaceutically acceptable carrier (e.g., isotonic saline with serum albumim), or with carrier solution alone as a control. Test animals receive either 10, 100, 250, 500, 1000, or 5000 µg of a VEGF-C polypeptide via intra-arterial infusion, e.g., as described in Example 1. A second group of animals additionally receive an injection of the VEGF-C polypeptide 7 days later. The animals are sacrificed and histological examination performed as described in Example 1. Reduced I/M ratio in the VEGF-C-treated animals versus control animals provides evidence of the therapeutic efficacy of VEGF-C polypeptide treatment. Repetition of the experiment using various sustained-release VEGF-C formulations and materials as described above is expected to further enhance the therapeutic efficacy of the VEGF-C polypeptide. Moreover, a treatment regimen comprising the simultaneous administration of VEGF-C protein (to provide immediate therapy to the target vessel) with a VEGF-C transgene (to provide sustained therapy for several days or weeks) is specifically contemplated as a variation of the invention.

EXAMPLE 9

Anti-Stenosis/Anti-Restenosis Activity of VEGF-D

The procedures described in the preceding examples are repeated using a composition comprising a VEGF-D polynucleotide or VEGF-D polypeptide in lieu of the VEGF-C polynucleotide/polypeptide, to demonstrate the ability of VEGF-D to prevent stenosis or restenosis of a blood vessel.

While the present invention has been described in terms of specific embodiments, it is understood that variations and modifications will occur to those in the art, all of which are intended as aspects of the present invention. Accordingly, only such limitations as appear in the claims should be placed on the invention.

What is claimed is:

1. A method of treating a mammalian subject in need of treatment to inhibit stenosis or restenosis of a blood vessel, comprising the step of:
administering directly to the blood vessel a composition comprising a polynucleotide, the polynucleotide comprising a nucleotide sequence that encodes a polypeptide operatively linked to a promoter for expression of the polypeptide in cells of the blood vessel,
wherein the encoded polypeptide comprises an amino acid sequence selected from the group consisting of:
(a) the amino acid sequence of SEQ ID NO: 4; and
(b) a fragment of (a) wherein the fragment comprises amino acids 93-201 of SEQ ID NO: 4 and binds to and stimulates phosphorylation of VEGFR-2 or VEGFR-3, and
wherein said polypeptide expressed by the cells of the blood vessel inhibits stenosis or restenosis of said blood vessel.

2. The method of claim 1 wherein the polypeptide encoded by said polynucleotide comprises the fragment of SEQ ID NO: 4, said fragment comprising amino acids 93-201 of SEQ ID NO: 4.

3. The method of claim 1 or 2 wherein said mammalian subject is a human.

4. The method of claim 1 or 2 wherein said polynucleotide further comprises a nucleotide sequence encoding a secretory signal peptide, and wherein the sequence encoding the secretory signal peptide is operably linked to the promoter and connected in-frame with the sequence that encodes the polypeptide.

5. The method of claim 4 wherein said encoded polypeptide lacks amino acids 1 to 92 of SEQ ID NO: 4 and lacks amino acids 202 to 354 of SEQ ID NO: 4.

6. The method of claim 4 wherein the signal sequence is a heterologous signal sequence.

7. The method of claim 1 or 2 wherein the composition comprises a gene therapy vector comprising said polynucleotide, wherein the gene therapy vector is selected from the group consisting of a replication-deficient adenovirus, an adeno-associated virus, an adenovirus, a lipofectin-mediated gene transfer vector, a liposome, and a naked DNA plasmid.

8. The method of claim 7, wherein the composition is administered by a procedure or a device selected from the group consisting of a catheter mediated gene transfer, a balloon catheter, a coated catheter, a coated stent, and an extravascular collar.

9. The method of claim 7, wherein the vector comprises the replication deficient adenovirus administered at a titer of $10^7$-$10^{13}$ viral particles.

10. The method of claim 7 wherein the vector comprises the replication deficient adenovirus, and wherein the composition comprises the adenovirus administered at a titer of $10^9$-$10^{11}$ viral particles.

11. The method according to any one of claims 1 and 2, wherein the mammalian subject is a human subject in need of a surgery involving the blood vessel.

12. The method according to any one of claims 1 and 2 wherein the mammalian subject is a human subject and the polynucleotide is administered prophylactically to the blood vessel shortly before, and/or concurrently with and/or shortly after an angioplasty procedure or a procedure to perform a vascular graft.

13. The method according to claim 12, wherein the polynucleotide is administered with a device employed in the angioplasty selected from the group consisting of a catheter, a stent, an expandable elastic membrane, and combinations thereof.

14. The method according to claim 12, wherein the polynucleotide is administered with a device used in a vascular graft procedure.

15. The method according to claim 14, wherein the device is an extravascular collar.

16. The method of claim 1, wherein the encoded polypeptide comprises the amino acid sequence of SEQ ID NO: 4.

17. The method of claim 1 polypeptide comprises the amino acid sequence of SEQ ID NO: 4.

18. The method of claim 1 wherein the composition comprises a gene therapy vector, said gene therapy vector comprising said polynucleotide.

19. The method of claim 18 wherein the gene therapy vector comprises a replication deficient adenovirus, said adenovirus comprising the polynucleotide operably linked to the promoter and flanked by adenoviral polynucleotide sequences.

20. The method of any one of claim 17, or 18 wherein said mammalian subject is a human.

21. A method of treating a mammalian subject in need of treatment to inhibit restenosis of a blood vessel, comprising:
   identifying a mammalian subject with the blood vessel wherein the vessel has been treated for stenosis or will be treated for the stenosis; and
   directly administering to the mammalian subject at the site of the blood vessel a composition comprising a polynucleotide operatively linked to a promoter for expression of a polypeptide encoded by the polynucleotide to promote expression of the polypeptide in cells of the blood vessel,
   wherein the encoded polypeptide comprises an amino acid sequence selected from the group consisting of:
   (a) the amino acid sequence of SEQ ID NO: 4; and
   (b) a fragment of (a) wherein the fragment comprises amino acids 93-201 of SEQ ID NO: 4 and binds to and stimulates phosphorylation of VEGFR-2 or VEGFR-3, and
   wherein the polypeptide expressed by the cells of the blood vessel inhibits restenosis of said blood vessel.

22. The method of claim 21 wherein the composition comprises a gene therapy vector comprising said polynucleotide, wherein the gene therapy vector is selected from the group consisting of a replication-deficient adenovirus, an adeno-associated virus, an adenovirus, a lipofectin-mediated gene transfer vector, a liposome, and a naked DNA plasmid.

23. The method of claim 21 wherein the administering is performed via a device selected from the group consisting of an intravascular stent; an intravascular catheter; a combination of an intravascular stent and catheter; an extravascular collar; and an elastomeric membrane adapted to cover a surface of an intravascular stent or catheter.

24. A method of treating a mammalian subject to inhibit stenosis or restenosis of a blood vessel graft, comprising:
   administering to the mammalian subject at the site of the blood vessel graft a composition comprising a polynucleotide encoding a polypeptide operatively linked to a promoter for expression of the polypeptide encoded by the polynucleotide to promote expression of the polypeptide in blood vessel cells,
   wherein the encoded polypeptide comprises an amino acid sequence selected from the group consisting of:
   (a) the amino acid sequence of SEQ ID NO: 4; and
   (b) a fragment of (a) wherein the fragment comprises amino acids 93-201 of SEQ ID NO: 4 and binds to and stimulates phosphorylation of VEGFR-2 or VEGFR-3, and
   wherein expression of said polynucleotide in said blood vessel cells inhibits stenosis of said blood vessel graft.

25. The method according to claim 24, wherein the composition comprises a gene therapy vector comprising said polynucleotide, wherein the gene therapy vector is selected from the group consisting of a replication-deficient adenovirus, an adeno-associated virus, an adenovirus, a lipofectin-mediated gene transfer vector, a liposome, and a naked DNA plasmid.

26. The method of any one of claim 21, or 24, wherein the polypeptide encoded by said polynucleotide comprises the fragment of SEQ ID NO: 4, said fragment comprising amino acids 93-201 of SEQ ID NO: 4.

27. The method according to claim 26, wherein the mammalian subject is a human.

28. The method of any one of claim 21, or 24, wherein the composition is administered by a procedure or device selected from the group consisting of catheter mediated gene transfer, balloon catheter, coated catheter, coated stent, and extravascular collar.

29. An improvement in a medical device designed to contact a surface of a blood vessel in the course of surgery to inhibit stenosis or restenosis of the blood vessel, said improvement comprising integrating into the device a composition effective to prevent stenosis or restenosis, said composition comprising a polynucleotide operatively linked to a promoter for expression of a polypeptide encoded by the polynucleotide in cells of blood vessels,
   wherein the device is selected from the group consisting of an intravascular stent; an intravascular catheter; a combination of an intravascular stent and catheter; an extravascular collar; and an elastomeric membrane adapted to cover a surface of an intravascular stent or catheter; and
   wherein the encoded polypeptide comprises an amino acid sequence selected from the group consisting of:
   (a) the amino acid sequence of SEQ ID NO: 4; and
   (b) a fragment of (a) wherein the fragment comprises amino acids 93-201 of SEQ ID NO: 4 and binds to and stimulates phosphorylation of VEGFR-2 or VEGFR-3.

30. An improvement in a medical device designed to contact a surface of a blood vessel in the course of surgery to inhibit stenosis or restenosis of the blood vessel, said improvement comprising integrating into the device a composition effective to inhibit stenosis or restenosis, said composition comprising a polynucleotide operatively linked to a promoter for expression of a polypeptide encoded by the polynucleotide in cells of blood vessels,
   wherein the device is selected from the group consisting of an intravascular stent; an intravascular catheter; a combination of an intravascular stent and catheter; an extravascular collar; and an elastomeric membrane adapted to cover a surface of an intravascular stent or catheter; and
   wherein the polynucleotide comprises a nucleotide sequence that encodes a polypeptide that comprises amino acids 93 to 201 of SEQ ID NO: 4 and that binds and stimulates at least one receptor selected from the group consisting of human VEGFR-2 and VEGFR-3.

31. The improvement of claim 29 or 30 wherein the composition comprises a gene therapy vector comprising said polynucleotide, wherein the gene therapy vector is selected from the group consisting of a replication-deficient adenovirus, an adeno-associated virus, an adenovirus, a lipofectin-mediated gene transfer vector, a liposome, and a naked DNA plasmid.

32. The improvement of claim 29 or 30, wherein the device is selected from the group consisting of the intravascular stent, the intravascular catheter, and the combination thereof.

33. The improvement of claim 29 or 30, wherein the device comprises the extravascular collar.

34. The improvement of claim 29 or 30, wherein the device comprises the elastomeric membrane adapted to cover a surface of an intravascular stent or catheter.

35. A medical device comprising an endovascular stent having an outer surface for contacting a surface of a blood vessel, and a composition on said outer surface, said composition comprising a polynucleotide operatively linked to a promoter for expression of a polypeptide encoded by the polynucleotide in cells of blood vessels,
  wherein the encoded polypeptide comprises an amino acid sequence selected from the group consisting of:
    (a) the amino acid sequence of SEQ ID NO: 4; and
    (b) a fragment of (a) wherein the fragment comprises amino acids 93-201 of SEQ ID NO: 4 and binds to and stimulates phosphorylation of VEGFR-2 or VEGFR-3.

36. A medical device comprising a catheter having an outer surface for contacting a surface of a blood vessel, and a composition on said outer surface, said composition comprising a polynucleotide operatively linked to a promoter for expression of a polypeptide encoded by the polynucleotide in cells of blood vessels,
  wherein the encoded polypeptide comprises an amino acid sequence selected from the group consisting of:
    (a) the amino acid sequence of SEQ ID NO: 4; and
    (b) a fragment of (a) wherein the fragment comprises amino acids 93-201 of SEQ ID NO: 4 and binds to and stimulates phosphorylation of VEGFR-2 or VEGFR-3.

37. A medical device comprising a balloon catheter having a void for holding a composition for delivery to the interior of a blood vessel, and a composition contained in the void, the composition comprising a polynucleotide operatively linked to a promoter for expression of a polypeptide encoded by the polynucleotide in cells of blood vessels,
  wherein the encoded polypeptide comprises an amino acid sequence selected from the group consisting of:
    (a) the amino acid sequence of SEQ ID NO: 4; and
    (b) a fragment of (a) wherein the fragment comprises amino acids 93-201 of SEQ ID NO: 4 and binds to and stimulates phosphorylation of VEGFR-2 or VEGFR-3.

38. The medical device of any one of claims 35-37 wherein the composition comprises a gene therapy vector comprising said polynucleotide, wherein the gene therapy vector is selected from the group consisting of a replication-deficient adenovirus, an adeno-associated virus, an adenovirus, a lipofectin-mediated gene transfer vector, a liposome, and a naked DNA plasmid.

39. A medical device comprising an extravascular collar comprising a composition for delivery to a blood vessel, the composition comprising a polynucleotide operatively linked to a promoter for expression of a polypeptide encoded by the polynucleotide in cells of the blood vessel,
  wherein the encoded polypeptide comprises an amino acid sequence selected from the group consisting of:
    (a) the amino acid sequence of SEQ ID NO: 4; and
    (b) a fragment of (a) wherein the fragment comprises amino acids 93-201 of SEQ ID NO: 4 and binds to and stimulates phosphorylation of VEGFR-2 or VEGFR-3.

40. The device of claim 39 wherein the extravascular collar is coated with, impregnated with or encapsulates the composition.

41. The device of claim 39 comprising a body adapted to provide a seal around the blood vessel and to define a reservoir for holding the composition.

42. The device of claim 39 wherein the composition comprises a gene therapy vector comprising said polynucleotide, wherein the gene therapy vector is selected from the group consisting of a replication-deficient adenovirus, an adeno-associated virus, an adenovirus, a lipofectin-mediated gene transfer vector, a liposome, and a naked DNA plasmid.

43. The device of claim 39 wherein said encoded polypeptide lacks amino acids 1 to 92 of SEQ ID NO: 4 and lacks amino acids 202 to 354 of SEQ ID NO: 4.

44. The device of claim 39, wherein the polynucleotide comprises a nucleotide sequence that encodes the polypeptide comprising the fragment of SEQ ID NO: 4 that comprises amino acids 93-201 of SEQ ID NO: 4 and further encodes a secretory signal peptide, wherein the sequence of the secretory signal peptide is a heterologous sequence, and wherein the polynucleotide sequence encoding the secretory signal peptide is operably linked to the promoter and is connected in-frame with the sequence that encodes the polypeptide.

45. The device or the improvement of any one of claim 29, 35, 36, 37, or 39, wherein the polypeptide comprises the fragment of SEQ ID NO: 4, wherein the fragment comprises amino acids 93-201 of SEQ ID NO: 4.

46. The device or the improvement of any one of claims 29, 35, 36, 37 or 39, wherein the VEGF-D polypeptide comprises amino acids 1-354 of SEQ ID NO: 4.

\* \* \* \* \*

```
                          SEQUENCE LISTING

<160> NUMBER OF SEQ ID NOS: 18

<210> SEQ ID NO 1
<211> LENGTH: 1997
<212> TYPE: DNA
<213> ORGANISM: Homo sapiens
<220> FEATURE:
<221> NAME/KEY: CDS
<222> LOCATION: (352)..(1608)

<400> SEQUENCE: 1
cccgccccgc ctctccaaaa agctacaccg acgcggaccg cggcggcgtc ctccctcgcc      60
ctcgcttcac ctcgcgggct ccgaatgcgg ggagctcgga tgtccggttt cctgtgaggc     120
ttttacctga cacccgccgc ctttcccgg cactggctgg gagggcgccc tgcaaagttg     180
ggaacgcgga gccccggacc cgctcccgcc gcctccggct cgcccagggg gggtcgccgg     240
```

```
gaggagcccg ggggagaggg accaggaggg gcccgcggcc tcgcaggggc gcccgcgccc        300
ccacccctgc cccgccagc  ggaccggtcc cccaccccg  gtccttccac c atg cac        357
                                                        Met His
                                                         1 ttg ctg ggc ttc ttc tct gtg gcg tgt tct ctc gcc gct gcg ctg              405
Leu Leu Gly Phe Phe Ser Val Ala Cys Ser Leu Leu Ala Ala Ala Leu
         5                  10                  15 ctc ccg ggt cct cgc gag gcg ccc gcc gcc gcc gcc ttc gag tcc              453
Leu Pro Gly Pro Arg Glu Ala Pro Ala Ala Ala Ala Phe Glu Ser
         20                  25                  30 gga ctc gac ctc tcg gac gcg gag ccc gac gcg ggc gag gcc acg gct          501
Gly Leu Asp Leu Ser Asp Ala Glu Pro Asp Ala Gly Glu Ala Thr Ala
35              40                  45                  50 tat gca agc aaa gat ctg gag gag cag tta cgg tct gtg tcc agt gta          549
Tyr Ala Ser Lys Asp Leu Glu Glu Gln Leu Arg Ser Val Ser Ser Val
                55                  60                  65 gat gaa ctc atg act gta ctc tac cca gaa tat tgg aaa atg tac aag          597
Asp Glu Leu Met Thr Val Leu Tyr Pro Glu Tyr Trp Lys Met Tyr Lys
            70                  75                  80 tgt cag cta agg aaa gga ggc tgg caa cat aac aga gaa cag gcc aac          645
Cys Gln Leu Arg Lys Gly Gly Trp Gln His Asn Arg Glu Gln Ala Asn
        85                  90                  95 ctc aac tca agg aca gaa gag act ata aaa ttt gct gca gca cat tat          693
Leu Asn Ser Arg Thr Glu Glu Thr Ile Lys Phe Ala Ala Ala His Tyr
    100                 105                 110 aat aca gag atc ttg aaa agt att gat aat gag tgg aga aag act caa          741
Asn Thr Glu Ile Leu Lys Ser Ile Asp Asn Glu Trp Arg Lys Thr Gln
115                 120                 125                 130 tgc atg cca cgg gag gtg tgt ata gat gtg ggg aag gag ttt gga gtc          789
Cys Met Pro Arg Glu Val Cys Ile Asp Val Gly Lys Glu Phe Gly Val
                135                 140                 145 gcg aca aac acc ttc ttt aaa cct cca tgt gtg tcc gtc tac aga tgt          837
Ala Thr Asn Thr Phe Phe Lys Pro Pro Cys Val Ser Val Tyr Arg Cys
            150                 155                 160 ggg ggt tgc tgc aat agt gag ggg ctg cag tgc atg aac acc agc acg          885
Gly Gly Cys Cys Asn Ser Glu Gly Leu Gln Cys Met Asn Thr Ser Thr
        165                 170                 175 agc tac ctc agc aag acg tta ttt gaa att aca gtg cct ctc tct caa          933
Ser Tyr Leu Ser Lys Thr Leu Phe Glu Ile Thr Val Pro Leu Ser Gln
    180                 185                 190 ggc ccc aaa cca gta aca atc agt ttt gcc aat cac act tcc tgc cga          981
Gly Pro Lys Pro Val Thr Ile Ser Phe Ala Asn His Thr Ser Cys Arg
195                 200                 205                 210 tgc atg tct aaa ctg gat gtt tac aga caa gtt cat tcc att att aga          1029
Cys Met Ser Lys Leu Asp Val Tyr Arg Gln Val His Ser Ile Ile Arg
                215                 220                 225 cgt tcc ctg cca gca aca cta cca cag tgt cag gca gcg aac aag acc          1077
Arg Ser Leu Pro Ala Thr Leu Pro Gln Cys Gln Ala Ala Asn Lys Thr
            230                 235                 240 tgc ccc acc aat tac atg tgg aat aat cac atc tgc aga tgc ctg gct          1125
Cys Pro Thr Asn Tyr Met Trp Asn Asn His Ile Cys Arg Cys Leu Ala
        245                 250                 255 cag gaa gat ttt atg ttt tcc tcg gat gct gga gat gac tca aca gat          1173
Gln Glu Asp Phe Met Phe Ser Ser Asp Ala Gly Asp Asp Ser Thr Asp
    260                 265                 270 gga ttc cat gac atc tgt gga cca aac aag gag ctg gat gaa gag acc          1221
Gly Phe His Asp Ile Cys Gly Pro Asn Lys Glu Leu Asp Glu Glu Thr
275                 280                 285                 290 tgt cag tgt gtc tgc aga gcg ggg ctt cgg cct gcc agc tgt gga ccc          1269
```

```
              Cys Gln Cys Val Cys Arg Ala Gly Leu Arg Pro Ala Ser Cys Gly Pro
                          295                 300                 305 cac aaa gaa cta gac aga aac tca tgc cag tgt gtc tgt aaa aac aaa           1317
His Lys Glu Leu Asp Arg Asn Ser Cys Gln Cys Val Cys Lys Asn Lys
                310                 315                 320 ctc ttc ccc agc caa tgt ggg gcc aac cga gaa ttt gat gaa aac aca           1365
Leu Phe Pro Ser Gln Cys Gly Ala Asn Arg Glu Phe Asp Glu Asn Thr
                325                 330                 335 tgc cag tgt gta tgt aaa aga acc tgc ccc aga aat caa ccc cta aat           1413
Cys Gln Cys Val Cys Lys Arg Thr Cys Pro Arg Asn Gln Pro Leu Asn
            340                 345                 350 cct gga aaa tgt gcc tgt gaa tgt aca gaa agt cca cag aaa tgc ttg           1461
Pro Gly Lys Cys Ala Cys Glu Cys Thr Glu Ser Pro Gln Lys Cys Leu
355                 360                 365                 370 tta aaa gga aag aag ttc cac cac caa aca tgc agc tgt tac aga cgg           1509
Leu Lys Gly Lys Lys Phe His His Gln Thr Cys Ser Cys Tyr Arg Arg
                375                 380                 385 cca tgt acg aac cgc cag aag gct tgt gag cca gga ttt tca tat agt           1557
Pro Cys Thr Asn Arg Gln Lys Ala Cys Glu Pro Gly Phe Ser Tyr Ser
                390                 395                 400 gaa gaa gtg tgt cgt tgt gtc cct tca tat tgg aaa aga cca caa atg           1605
Glu Glu Val Cys Arg Cys Val Pro Ser Tyr Trp Lys Arg Pro Gln Met
            405                 410                 415 agc taagattgta ctgttttcca gttcatcgat tttctattat ggaaaactgt                1658
Ser gttgccacag tagaactgtc tgtgaacaga gagaccttg tgggtccatg ctaacaaga           1718 caaaagtctg tctttcctga accatgtgga taactttaca gaaatggact ggagctcatc        1778 tgcaaaggc ctcttgtaaa gactggtttt ctgccaatga ccaaacagcc aagattttcc         1838
tcttgtgatt tctttaaaag aatgactata taatttattt ccactaaaaa tattgtttct        1898
gcattcattt ttatagcaac aacaattggt aaaactcact gtgatcaata tttttatatc        1958
atgcaaaata tgtttaaaat aaaatgaaaa ttgtattat                               1997

<210> SEQ ID NO 2
<211> LENGTH: 419
<212> TYPE: PRT
<213> ORGANISM: Homo sapiens

<400> SEQUENCE: 2

Met His Leu Leu Gly Phe Phe Ser Val Ala Cys Ser Leu Leu Ala Ala
  1               5                   10                  15

Ala Leu Leu Pro Gly Pro Arg Glu Ala Pro Ala Ala Ala Ala Ala Phe
                20                  25                  30

Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
        50                  55                  60

Ser Val Asp Glu Leu Met Thr Val Leu Tyr Pro Glu Tyr Trp Lys Met
 65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140
```

```
Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
            165                 170                 175

Ser Thr Ser Tyr Leu Ser Lys Thr Leu Phe Glu Ile Thr Val Pro Leu
                180                 185                 190

Ser Gln Gly Pro Lys Pro Val Thr Ile Ser Phe Ala Asn His Thr Ser
            195                 200                 205

Cys Arg Cys Met Ser Lys Leu Asp Val Tyr Arg Gln Val His Ser Ile
        210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 3
<211> LENGTH: 2029
<212> TYPE: DNA
<213> ORGANISM: Homo sapiens
<220> FEATURE:
<221> NAME/KEY: CDS
<222> LOCATION: (411)..(1475)

<400> SEQUENCE: 3
gttgggttcc agctttctgt agctgtaagc attggtggcc acaccacctc cttacaaagc      60
aactagaacc tgcggcatac attggagaga ttttttttaat tttctggaca tgaagtaaat     120
ttagagtgct ttctaatttc aggtagaaga catgtccacc ttctgattat ttttggagaa     180
cattttgatt ttttcatct ctctctcccc acccctaaga ttgtgcaaaa aaagcgtacc     240
ttgcctaatt gaataatt cattggattt tgatcagaac tgattattg gttttctgtg      300 tgaagttttg aggtttcaaa ctttccttct ggagaatgcc ttttgaaaca attttctcta     360
gctgcctgat gtcaactgct tagtaatcag tggatattga aatattcaaa atg tac       416
                                                        Met Tyr
                                                          1
```

| | | | | | | | | | | | | | | | | |
|---|---|---|---|---|---|---|---|---|---|---|---|---|---|---|---|---|
| aga | gag | tgg | gta | gtg | gtg | aat | gtt | ttc | atg | atg | ttg | tac | gtc | cag | ctg | 464 |
| Arg | Glu | Trp | Val | Val | Val | Asn | Val | Phe | Met | Met | Leu | Tyr | Val | Gln | Leu | |
| | | 5 | | | | 10 | | | | | 15 | | | | | |
| gtg | cag | ggc | tcc | agt | aat | gaa | cat | gga | cca | gtg | aag | cga | tca | tct | cag | 512 |
| Val | Gln | Gly | Ser | Ser | Asn | Glu | His | Gly | Pro | Val | Lys | Arg | Ser | Ser | Gln | |
| | 20 | | | | | 25 | | | | | 30 | | | | | |
| tcc | aca | ttg | gaa | cga | tct | gaa | cag | cag | atc | agg | gct | gct | tct | agt | ttg | 560 |
| Ser | Thr | Leu | Glu | Arg | Ser | Glu | Gln | Gln | Ile | Arg | Ala | Ala | Ser | Ser | Leu | |
| 35 | | | | | 40 | | | | | 45 | | | | | 50 | |
| gag | gaa | cta | ctt | cga | att | act | cac | tct | gag | gac | tgg | aag | ctg | tgg | aga | 608 |
| Glu | Glu | Leu | Leu | Arg | Ile | Thr | His | Ser | Glu | Asp | Trp | Lys | Leu | Trp | Arg | |
| | | | | 55 | | | | | 60 | | | | | 65 | | |
| tgc | agg | ctg | agg | ctc | aaa | agt | ttt | acc | agt | atg | gac | tct | cgc | tca | gca | 656 |
| Cys | Arg | Leu | Arg | Leu | Lys | Ser | Phe | Thr | Ser | Met | Asp | Ser | Arg | Ser | Ala | |
| | | | 70 | | | | | 75 | | | | | 80 | | | |
| tcc | cat | cgg | tcc | act | agg | ttt | gcg | gca | act | ttc | tat | gac | att | gaa | aca | 704 |
| Ser | His | Arg | Ser | Thr | Arg | Phe | Ala | Ala | Thr | Phe | Tyr | Asp | Ile | Glu | Thr | |
| | | 85 | | | | | 90 | | | | | 95 | | | | |
| cta | aaa | gtt | ata | gat | gaa | gaa | tgg | caa | aga | act | cag | tgc | agc | cct | aga | 752 |
| Leu | Lys | Val | Ile | Asp | Glu | Glu | Trp | Gln | Arg | Thr | Gln | Cys | Ser | Pro | Arg | |
| | 100 | | | | | 105 | | | | | 110 | | | | | |
| gaa | acg | tgc | gtg | gag | gtg | gcc | agt | gag | ctg | ggg | aag | agt | acc | aac | aca | 800 |
| Glu | Thr | Cys | Val | Glu | Val | Ala | Ser | Glu | Leu | Gly | Lys | Ser | Thr | Asn | Thr | |
| 115 | | | | | 120 | | | | | 125 | | | | | 130 | |
| ttc | ttc | aag | ccc | cct | tgt | gtg | aac | gtg | ttc | cga | tgt | ggt | ggc | tgt | tgc | 848 |
| Phe | Phe | Lys | Pro | Pro | Cys | Val | Asn | Val | Phe | Arg | Cys | Gly | Gly | Cys | Cys | |
| | | | | 135 | | | | | 140 | | | | | 145 | | |
| aat | gaa | gag | agc | ctt | atc | tgt | atg | aac | acc | agc | acc | tcg | tac | att | tcc | 896 |
| Asn | Glu | Glu | Ser | Leu | Ile | Cys | Met | Asn | Thr | Ser | Thr | Ser | Tyr | Ile | Ser | |
| | | | 150 | | | | | 155 | | | | | 160 | | | |
| aaa | cag | ctc | ttt | gag | ata | tca | gtg | cct | ttg | aca | tca | gta | cct | gaa | tta | 944 |
| Lys | Gln | Leu | Phe | Glu | Ile | Ser | Val | Pro | Leu | Thr | Ser | Val | Pro | Glu | Leu | |
| | | 165 | | | | | 170 | | | | | 175 | | | | |
| gtg | cct | gtt | aaa | gtt | gcc | aat | cat | aca | ggt | tgt | aag | tgc | ttg | cca | aca | 992 |
| Val | Pro | Val | Lys | Val | Ala | Asn | His | Thr | Gly | Cys | Lys | Cys | Leu | Pro | Thr | |
| | 180 | | | | | 185 | | | | | 190 | | | | | |
| gcc | ccc | cgc | cat | cca | tac | tca | att | atc | aga | aga | tcc | atc | cag | atc | cct | 1040 |
| Ala | Pro | Arg | His | Pro | Tyr | Ser | Ile | Ile | Arg | Arg | Ser | Ile | Gln | Ile | Pro | |
| 195 | | | | | 200 | | | | | 205 | | | | | 210 | |
| gaa | gaa | gat | cgc | tgt | tcc | cat | tcc | aag | aaa | ctc | tgt | cct | att | gac | atg | 1088 |
| Glu | Glu | Asp | Arg | Cys | Ser | His | Ser | Lys | Lys | Leu | Cys | Pro | Ile | Asp | Met | |
| | | | | 215 | | | | | 220 | | | | | 225 | | |
| cta | tgg | gat | agc | aac | aaa | tgt | aaa | tgt | gtt | ttg | cag | gag | gaa | aat | cca | 1136 |
| Leu | Trp | Asp | Ser | Asn | Lys | Cys | Lys | Cys | Val | Leu | Gln | Glu | Glu | Asn | Pro | |
| | | | 230 | | | | | 235 | | | | | 240 | | | |
| ctt | gct | gga | aca | gaa | gac | cac | tct | cat | ctc | cag | gaa | cca | gct | ctc | tgt | 1184 |
| Leu | Ala | Gly | Thr | Glu | Asp | His | Ser | His | Leu | Gln | Glu | Pro | Ala | Leu | Cys | |
| | | 245 | | | | | 250 | | | | | 255 | | | | |
| ggg | cca | cac | atg | atg | ttt | gac | gaa | gat | cgt | tgc | gag | tgt | gtc | tgt | aaa | 1232 |
| Gly | Pro | His | Met | Met | Phe | Asp | Glu | Asp | Arg | Cys | Glu | Cys | Val | Cys | Lys | |
| | 260 | | | | | 265 | | | | | 270 | | | | | |
| aca | cca | tgt | ccc | aaa | gat | cta | atc | cag | cac | ccc | aaa | aac | tgc | agt | tgc | 1280 |
| Thr | Pro | Cys | Pro | Lys | Asp | Leu | Ile | Gln | His | Pro | Lys | Asn | Cys | Ser | Cys | |
| 275 | | | | | 280 | | | | | 285 | | | | | 290 | |
| ttt | gag | tgc | aaa | gaa | agt | ctg | gag | acc | tgc | tgc | cag | aag | cac | aag | cta | 1328 |
| Phe | Glu | Cys | Lys | Glu | Ser | Leu | Glu | Thr | Cys | Cys | Gln | Lys | His | Lys | Leu | |
| | | | | 295 | | | | | 300 | | | | | 305 | | |
| ttt | cac | cca | gac | acc | tgc | agc | tgt | gag | gac | aga | tgc | ccc | ttt | cat | acc | 1376 |
| Phe | His | Pro | Asp | Thr | Cys | Ser | Cys | Glu | Asp | Arg | Cys | Pro | Phe | His | Thr | |
| | | | 310 | | | | | 315 | | | | | 320 | | | |

-continued

```
aga cca tgt gca agt ggc aaa aca gca tgt gca aag cat tgc cgc ttt     1424
Arg Pro Cys Ala Ser Gly Lys Thr Ala Cys Ala Lys His Cys Arg Phe
        325                 330                 335 cca aag gag aaa agg gct gcc cag ggg ccc cac agc cga aag aat cct     1472
Pro Lys Glu Lys Arg Ala Ala Gln Gly Pro His Ser Arg Lys Asn Pro
    340                 345                 350 tga ttcagcgttc caagttcccc atccctgtca ttttaacag catgctgctt           1525 tgccaagttg ctgtcactgt ttttttccca ggtgttaaaa aaaaaatcca ttttacacag   1585
caccacagtg aatccagacc aaccttccat tcacaccagc taaggagtcc ctggttcatt   1645
gatggatgtc ttctagctgc agatgcctct gcgcaccaag gaatggagag gaggggaccc   1705
atgtaatcct tttgtttagt tttgttttg ttttttggtg aatgagaaag gtgtgctggt    1765
catggaatgg caggtgtcat atgactgatt actcagagca gatgaggaaa actgtagtct   1825
ctgagtcctt tgctaatcgc aactcttgtg aattattctg attcttttt atgcagaatt    1885 tgattcgtat gatcagtact gactttctga ttactgtcca gcttatagtc ttccagttta   1945
atgaactacc atctgatgtt tcatatttaa gtgtatttaa agaaaataaa caccattatt   2005
caagccaaaa aaaaaaaaaa aaaa                                          2029
```

<210> SEQ ID NO 4
<211> LENGTH: 354
<212> TYPE: PRT
<213> ORGANISM: Homo sapiens

<400> SEQUENCE: 4

```
Met Tyr Arg Glu Trp Val Val Asn Val Phe Met Met Leu Tyr Val
  1               5                  10                  15

Gln Leu Val Gln Gly Ser Ser Asn Glu His Gly Pro Val Lys Arg Ser
             20                  25                  30

Ser Gln Ser Thr Leu Glu Arg Ser Glu Gln Gln Ile Arg Ala Ala Ser
         35                  40                  45

Ser Leu Glu Glu Leu Leu Arg Ile Thr His Ser Glu Asp Trp Lys Leu
     50                  55                  60

Trp Arg Cys Arg Leu Arg Leu Lys Ser Phe Thr Ser Met Asp Ser Arg
 65                  70                  75                  80

Ser Ala Ser His Arg Ser Thr Arg Phe Ala Ala Thr Phe Tyr Asp Ile
                 85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
```

```
                    225                 230                 235                 240

Asn Pro Leu Ala Gly Thr Glu Asp His Ser His Leu Gln Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
                340                 345                 350

Asn Pro

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 5
ttggaggcct aggcttttgc                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
atactgtcgt cgtcccctca                                                    20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 7
ggtagaagac cccaaggact tt                                                 22

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 8
cgccattcgc cattcag                                                       17

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: primer
```

```
<400> SEQUENCE: 9
ctgcttactg gcttatcg                                                      18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 10
cctgttctct gttatgttgc                                                    20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 11
tctccaaaaa gctacaccg                                                     19

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 12
caagtgcatg gtggaagg                                                      18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 13
tcgatccatg aactttctgc                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 14
ttcgtttaac tcaagctgcc                                                    20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 15
gaccctggct ttactgctg                                                     19

<210> SEQ ID NO 16
<211> LENGTH: 20
```

<212> TYPE: DNA
<213> ORGANISM: Artificial Sequence
<220> FEATURE:
<223> OTHER INFORMATION: Description of Artificial Sequence: primer

<400> SEQUENCE: 16
ggaacattta cacgtctgcg                                                     20

<210> SEQ ID NO 17
<211> LENGTH: 2679
<212> TYPE: DNA
<213> ORGANISM: Artificial Sequence
<220> FEATURE:
<223> OTHER INFORMATION: Description of Artificial Sequence: chimeric
      sequence in which CMV promoter sequence is ligated
      to Homo sapien VEGF-C sequence

<400> SEQUENCE: 17

```
cgttgacatt gattattgac tagttattaa tagtaatcaa ttacggggtc attagttcat      60
agcccatata tggagttccg cgttacataa cttacggtaa atggcccgcc tggctgaccg     120
cccaacgacc cccgcccatt gacgtcaata atgacgtatg ttcccatagt aacgccaata     180
gggactttcc attgacgtca atgggtggac tatttacggt aaactgccca cttggcagta     240
catcaagtgt atcatatgcc aagtacgccc cctattgacg tcaatgacgg taaatggccc     300
gcctggcatt atgcccagta catgacctta tgggactttc ctacttggca gtacatctac     360
gtattagtca tcgctattac catggtgatg cggttttggc agtacatcaa tgggcgtgga     420
tagcggtttg actcacgggg atttccaagt ctccacccca ttgacgtcaa tgggagtttg     480
ttttggcacc aaaatcaacg ggactttcca aatgtcgta acaactccgc cccattgacg     540
caaatgggcg gtaggcgtgt acggtgggag gtctatataa gcagagctct ctggctaact     600
agagaaccca ctgcttactg gcttatcgaa attaatacga ctcactatag ggagacccaa     660
gctggctagc gtttaaactt aacccgcccc gcctctccaa aaagctacac cgacgcggac     720
cgcggcggcg tcctccctcg ccctcgcttc acctcgcggg ctccgaatgc ggggagctcg     780
gatgtccggt ttcctgtgag gcttttacct gacacccgcc gcctttcccc ggcactggct     840
gggagggcgc cctgcaaagt tgggaacgcg gagccccgga cccgctcccg ccgcctccgg     900
ctcgcccagg gggggtcgcc gggaggagcc cggggagag ggaccaggag gggcccgcgg     960
cctcgcaggg gcgcccgcgc cccaccccct gccccgcca gcggaccggt cccccacccc    1020
cggtccttcc accatgcact tgctgggctt cttctctgtg gcgtgttctc tgctcgccgc    1080
tgcgctgctc ccgggtcctc gcgaggcgcc cgccgccgcc gccgccttcg agtccggact    1140
cgacctctcg gacgcggagc ccgacgcggg cgaggccacg gcttatgcaa gcaaagatct    1200
ggaggagcag ttacggtctg tgtccagtgt agatgaactc atgactgtac tctacccaga    1260
atattggaaa atgtacaagt gtcagctaag gaaaggaggc tggcaacata acagagaaca    1320
ggccaacctc aactcaagga cagaagagac tataaaattt gctgcagcac attataatac    1380
agagatcttg aaaagtattg ataatgagtg gagaaagact caatgcatgc cacgggaggt    1440
gtgtatagat gtggggaagg agtttggagt cgcgacaaac accttcttta acctccatg    1500 tgtgtccgtc tacagatgtg ggggttgctg caatagtgag gggctgcagt gcatgaacac    1560
cagcacgagc tacctcagca agacgttatt tgaaattaca gtgcctctct ctcaaggccc    1620
caaaccagta acaatcagtt ttgccaatca cacttcctgc cgatgcatgt ctaaactgga    1680
tgtttacaga caagttcatt ccattattag acgttccctg ccagcaacac taccacagtg    1740
tcaggcagcg aacaagacct gccccaccaa ttacatgtgg aataatcaca tctgcagatg    1800
```

```
cctggctcag gaagatttta tgttttcctc ggatgctgga gatgactcaa cagatggatt     1860
ccatgacatc tgtggaccaa acaaggagct ggatgaagag acctgtcagt gtgtctgcag     1920
agcggggctt cggcctgcca gctgtggacc ccacaaagaa ctagacagaa actcatgcca     1980
gtgtgtctgt aaaaacaaac tcttccccag ccaatgtggg gccaaccgag aatttgatga     2040
aaacacatgc cagtgtgtat gtaaaagaac ctgccccaga aatcaacccc taaatcctgg     2100
aaaatgtgcc tgtgaatgta cagaaagtcc acagaaatgc ttgttaaaag gaaagaagtt     2160
ccaccaccaa acatgcagct gttacagacg gccatgtacg aaccgccaga aggcttgtga     2220
gccaggattt tcatatagtg aagaagtgtg tcgttgtgtc ccttcatatt ggaaaagacc     2280
acaaatgagc taagattgta ctgttttcca gttcatcgat tttctattat ggaaaactgt     2340
gttgccacag tagaactgtc tgtgaacaga gagacccttg tgggtccatg ctaacaaaga     2400
caaaagtctg tctttcctga accatgtgga taactttaca gaaatggact ggagctcatc     2460
tgcaaaaggc ctcttgtaaa gactggtttt ctgccaatga ccaaacagcc aagattttcc     2520
tcttgtgatt tctttaaaag aatgactata taatttattt ccactaaaaa tattgtttct     2580
gcattcattt ttatagcaac aacaattggt aaaactcact gtgatcaata tttttatatc     2640
atgcaaaata tgtttaaaat aaaatgaaaa ttgtattat                            2679
```

<210> SEQ ID NO 18
<211> LENGTH: 2240
<212> TYPE: DNA
<213> ORGANISM: Mus musculus

<400> SEQUENCE: 18

```
tgtttagaag atgaaccgta agcctaggct agaactgagg gagcctacta ctcccacccT      60
tccgagggtt ggcggcagga ctgggcagct ggcctaccta cctttctgaa tgctagggta     120
ggtttgaatc accatgccgg cctggcccgc ttctgccccc attggcaccc tggcttcagt     180
tccctggcaa catctctgtg tgtgtgtgtg tgtgtgagag agagagatca ggaggaacaa     240
gggcctctgt ctgcccagca gttgtctctc cttcagggct ctgccagact acacagtgca     300
tacgtgggtt tccacaggtc gtctcactcc ccgccactga ctaactccag aactccaccc     360
ccgttctcag tgccacaaat ttggtgccaa attctctcca gagaagcctc tctgaaaact     420
tcccagagga tcccattcac cccagggccc tagctcctga tgactgcaga tcagacaagg     480
gctcagataa gcatactccc ccccccccgt aaccccctcc ccacatataa acctacagtt     540
atgcttccga ggtcaaacac gcaacttttt gggtgtgtgt gtatgtcaga aacacgcaat     600
tatttgggag ctcaaagtct gccgcactca agaatcatct ctcacccccT ttccaagacc     660
cgtgccattt gagcaagagt tggggtgtgc ataatgtagt cactaggggg cgctcggcca     720
tcacggggag atcgtaactt gggcgagccg agtctgcgtg agggaggacg cgtgtttcaa     780
tgtgagtgcg tgcatgctgt gtgtgtgtgt gtagtgtgtg tgtgaggtgg gggagaaagc     840 cagggggtcac tctagttgtc cctatcctca tacgttcctg ccagctctcc gccttccaac     900
ccctactttc tcctatatcc tgggaaaggg aattgtctta gaccctgtcc gcatataacc     960
tcactctcct gtctccctg attcccaata ctctgggatt cccagtgtgt tcctgagccc    1020
atttgaaggg gtgcacagat aatttgagg ccgtggaccc tggtaagggg tttagctttc    1080
catttcgcgg tagtggccta ggggctcccc gaaaggcggt gcctggctcc accagaccgt    1140
ccccggggcg ggtctgggcg gggcttgggg gtggagctag atttcctctt tttcttccac    1200
cgctgttacc ggtgagaagc gcagaggctt ggggcagccg agctgcagcg agcgcgcggc    1260
```

```
actggggcg agctgagcgg cggcagcgga gctctgtcgc gagacgcagc gacaaggcag    1320
actatcagcg gactcaccag cccgggagtc tgtgctctgg gatttgatat tcaaacctct    1380 taatttttt ttcttaaact gtattgtttt acgctttaat ttatttttgc ttcctattcc    1440
cctcttaaat cgtgccaacg gtttgaggag gttggttctt cactccctca aatcacttcg    1500
gattgtggaa atcagcagac gaaagaggta tcaagagctc cagagagaag tcaaggaaga    1560
gagagagaga ccggtcagag agagcgcgct ggcgagcgaa cagagagagg gacaggggca    1620
aagttgactt gaccttgctt ttgggggtga ccgccagagc gcggcgtgac ctccccttc    1680 gatcttgcat cggaccagtc gcgctgacgg acagacagac agacaccgcc cccagcccca    1740
gcgcccacct cctcgccggc gggctgccga cggtggacgc ggcggcgagc cgagaaaccg    1800
aagcccgcgc ccggaggcgg gtggaggggg tcggggctcg cgggattgca cggaaacttt    1860
tcgtccaact tctgggctct tctcgctccg tagtagccgt ggtctgcgcc gcaggagaca    1920
aaccgatccg gagctgggag aaggctagct cggccctgga gaggccgggg cccgagaaga    1980
gaggggagga aggaagagga gagggggcca cagtgggcgc tcggctctca ggagccgagc    2040
tcatggacgg gtgaggcggc cgtgtgcgca gacagtgctc cagccgcgcg cgcgcccag    2100 gccccggccc gggcctcggt tccagaaggg agaggagccc gccaaggcgc gcaagagagc    2160
gggctgcctc gcagtccgga gccggagaga gggagcgcga gccgccgcgg ccccggacgg    2220
cctccgaaac catgaacttt                                                2240
```